United States Patent
Wang

(10) Patent No.: US 10,111,708 B2
(45) Date of Patent: Oct. 30, 2018

(54) SYSTEM AND METHOD FOR LOCATING AND IDENTIFYING THE FUNCTIONAL NERVES INNERVATING THE WALL OF ARTERIES AND CATHETERS FOR SAME

(71) Applicant: SYMAP HOLDING LIMITED, Road Town, Tortola (VG)

(72) Inventor: Jie Wang, Englewood Cliffs, NJ (US)

(73) Assignee: SYMAP MEDICAL (SUZHOU), LTD (CN)

( * ) Notice: Subject to any disclaimer, the term of this patent is extended or adjusted under 35 U.S.C. 154(b) by 0 days.

(21) Appl. No.: 15/636,960

(22) Filed: Jun. 29, 2017

(65) Prior Publication Data
US 2017/0296265 A1    Oct. 19, 2017

Related U.S. Application Data

(63) Continuation of application No. 15/195,998, filed on Jun. 28, 2016, now Pat. No. 9,723,998, which is a
(Continued)

(51) Int. Cl.
*A61B 5/04*  (2006.01)
*A61B 18/14*  (2006.01)
(Continued)

(52) U.S. Cl.
CPC .......... *A61B 18/1492* (2013.01); *A61B 5/024* (2013.01); *A61B 5/0205* (2013.01);
(Continued)

(58) Field of Classification Search
CPC ..... A61B 5/0205; A61B 5/0215; A61B 5/024; A61B 5/04001; A61B 5/0538;
(Continued)

(56) References Cited

U.S. PATENT DOCUMENTS

| | | | |
|---|---|---|---|
| 8,702,619 B2 * | 4/2014 | Wang ................... | A61B 5/4893 600/554 |
| 9,014,821 B2 * | 4/2015 | Wang ................... | A61B 5/0205 607/117 |

(Continued)

*Primary Examiner* — Michael Carey
(74) *Attorney, Agent, or Firm* — Law Office of Albert Wai-Kit Chan, PLLC

(57) ABSTRACT

System and method for locating and identifying nerves innervating the wall of arteries such as the renal artery are disclosed. The present invention identifies areas on vessel walls that are innervated with nerves; provides indication on whether energy is delivered accurately to a targeted nerve; and provides immediate post-procedural assessment of the effect of energy delivered to the nerve. The method includes at least the steps to evaluate a change in physiological parameters after energy is delivered to an arterial wall; and to determine the type of nerve that the energy was directed to (none, sympathetic or parasympathetic) based on the evaluated results. The system includes at least a device for delivering energy to the wall of blood vessel; sensors for detecting physiological signals from a subject; and indicators to display results obtained using said method. Also provided are catheters for performing the mapping and ablating functions.

20 Claims, 28 Drawing Sheets

Related U.S. Application Data continuation of application No. 14/691,553, filed on Apr. 20, 2015, now Pat. No. 9,375,154, which is a continuation of application No. 14/241,061, filed as application No. PCT/IB2012/054310 on Aug. 24, 2012, now Pat. No. 9,014,821.

(60) Provisional application No. 61/609,565, filed on Mar. 12, 2012, provisional application No. 61/527,893, filed on Aug. 26, 2011.

(51) Int. Cl.

| | | |
|---|---|---|
| *A61B 5/0205* | (2006.01) | |
| *A61B 5/20* | (2006.01) | |
| *A61B 5/00* | (2006.01) | |
| *A61B 5/0215* | (2006.01) | |
| *A61B 5/024* | (2006.01) | |
| *A61B 5/053* | (2006.01) | |
| *A61B 18/24* | (2006.01) | |
| *A61N 7/02* | (2006.01) | |
| *A61B 18/00* | (2006.01) | |
| *A61B 18/18* | (2006.01) | |
| *A61N 1/36* | (2006.01) | |
| *A61N 7/00* | (2006.01) | |

(52) U.S. Cl.
CPC ........ *A61B 5/0215* (2013.01); *A61B 5/04001* (2013.01); *A61B 5/0538* (2013.01); *A61B 5/201* (2013.01); *A61B 5/4833* (2013.01); *A61B 5/4836* (2013.01); *A61B 5/4893* (2013.01); *A61B 5/6852* (2013.01); *A61B 5/6853* (2013.01); *A61B 18/24* (2013.01); *A61N 7/02* (2013.01); *A61B 18/18* (2013.01); *A61B 2018/00404* (2013.01); *A61B 2018/00434* (2013.01); *A61B 2018/00505* (2013.01); *A61B 2018/00511* (2013.01); *A61B 2018/00577* (2013.01); *A61B 2018/00642* (2013.01); *A61B 2018/00708* (2013.01); *A61B 2018/00791* (2013.01); *A61B 2018/00839* (2013.01); *A61B 2018/00875* (2013.01); *A61N 1/36117* (2013.01); *A61N 2007/003* (2013.01)

(58) Field of Classification Search
CPC ..... A61B 5/201; A61B 5/4833; A61B 5/4836; A61B 5/4893; A61B 5/6852; A61B 5/6853; A61B 18/1492; A61B 18/18; A61B 18/24; A61B 2018/00404; A61B 2018/00434; A61B 2018/00505; A61B 2018/00511; A61B 2018/00577; A61B 2018/00642; A61B 2018/00708; A61B 2018/00791; A61B 2018/00839; A61B 2018/00875; A61N 1/36117; A61N 7/02; A61N 2007/003
USPC ....... 600/300, 301; 606/32, 20, 27; 607/118, 607/117, 148, 149
See application file for complete search history.

(56) References Cited

U.S. PATENT DOCUMENTS

| | | | |
|---|---|---|---|
| 9,723,998 B2* | 8/2017 | Wang | .................. A61B 5/0205 |
| 9,743,845 B2* | 8/2017 | Wang | .................. A61B 5/0215 |
| 9,820,811 B2* | 11/2017 | Wang | ..................... A61B 5/024 |
| 2007/0135875 A1 | 6/2007 | Demarais et al. | |
| 2007/0255379 A1 | 11/2007 | Williams et al. | |
| 2012/0265198 A1* | 10/2012 | Crow | ................ A61B 18/1492 |
| | | | 606/41 |

\* cited by examiner

X > a    => sympathetic nerve
X < -b   => parasympathetic nerve
X = 0    => no functioning nerves where values of a and b were
determined empirically from a large
statistical group

3A

3B

3C

3D

3E

3F

3G

3H

3I

3J

4A

4B

4C

4D

4E

4F

5A

5B

6A

6B

6C

6D

7A

7B

9A

9B

9C

9D

10A

10B

10C

Effect of Stimulation on MAP in Pigs
(RRA, n=3)

10D

Effect of Stimulation on HR in Pigs
(RRA, n=3)

12A

12B

13A

13B

13C

13D

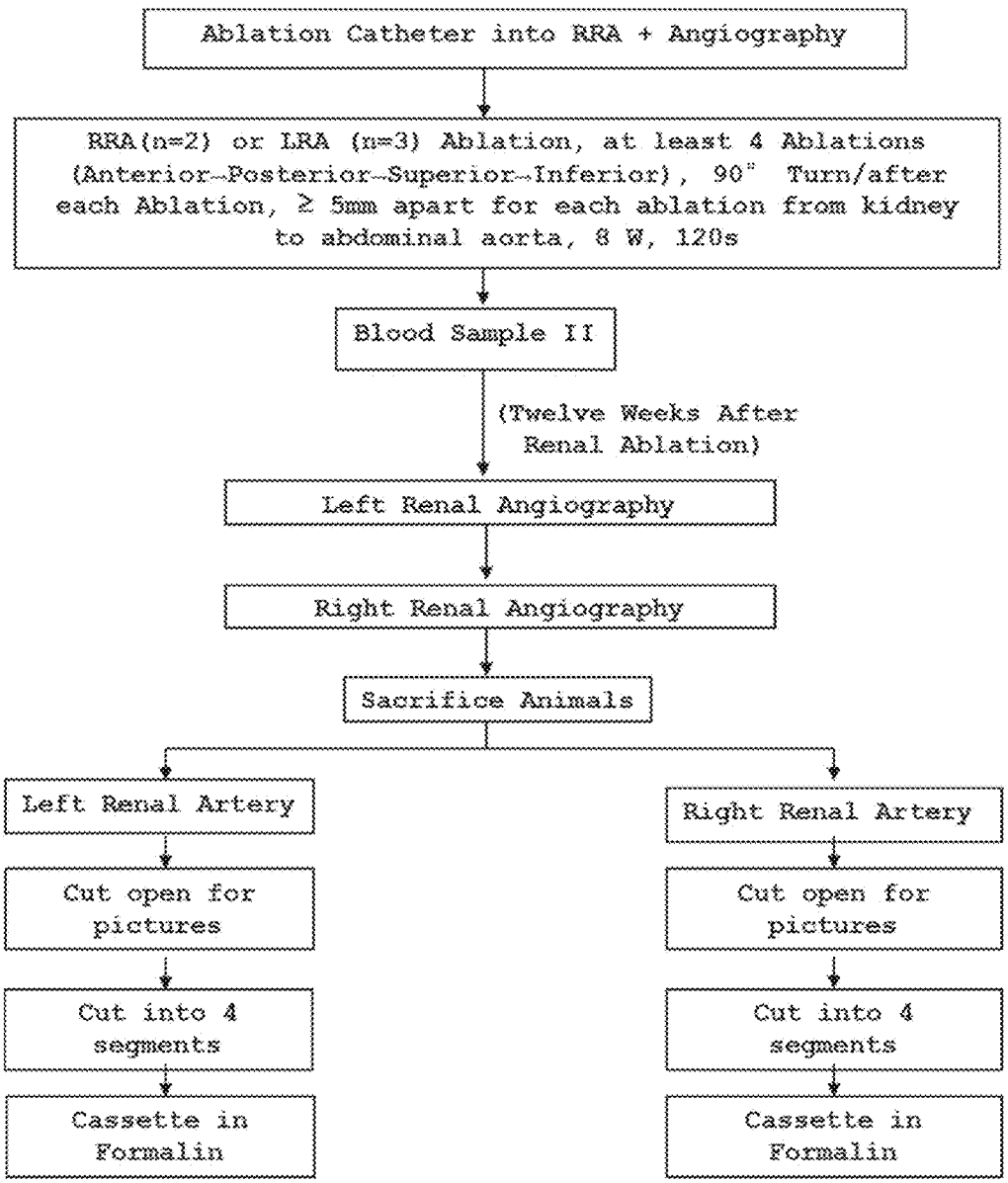

Histology Cassette Labeling:

LK1, LK2, LK3, LK4; RK1, RK2, RK3, RK4

SYSTEM AND METHOD FOR LOCATING AND IDENTIFYING THE FUNCTIONAL NERVES INNERVATING THE WALL OF ARTERIES AND CATHETERS FOR SAME

CROSS-REFERENCE TO RELATED APPLICATIONS

This application is a Continuation Application of U.S. Ser. No. 15/195,998, filed Jun. 28, 2016, published as US20160374568A1, now U.S. Pat. No. 9,723,998, which is a Continuation Application of U.S. Ser. No. 14/691,553, filed Apr. 20, 2015, published as US20150289770A1, now U.S. Pat. No. 9,375,154, which is a Continuation Application of U.S. Ser. No. 14/241,061, filed Feb 25, 2014, published as US20140213873A1, now U.S. Pat No. 9,014,821, which is the National Stage of International Application No. PCT/IB2012/054310, filed Aug. 24, 2012, published as WO2013030743A1, which claims priority of U.S. Ser. No. 61/609,565, filed Mar. 12, 2012 and U.S. Ser. No. 61/527,893, filed Aug. 26, 2011. The contents of the preceding applications are hereby incorporated in their entireties by reference into this application. Throughout this application, various publications are referenced. Disclosures of these publications in their entireties are hereby incorporated by reference into this application in order to more fully describe the state of the art to which this invention pertains.

FIELD OF THE INVENTION

This invention relates to a system and method for accurate and precise location and identification of areas innervated with sympathetic and parasympathetic related nerves on an arterial wall during and after an energy delivery process. This invention also relates to catheter systems specifically designed for use in renal nerve mapping and ablation.

BACKGROUND OF THE INVENTION

Congestive heart failure, hypertension, diabetes, and chronic renal failure have many different initial causes; however, all follow a common pathway in their progression to end-stage diseases. The common pathway is renal sympathetic nerve hyperactivity. Renal sympathetic nerves serve as the signal input pathway to higher sympathetic centers located in the spinal cord and brain via afferent renal nerve activity, increasing systemic sympathetic tone; meanwhile, through efferent activity, renal nerves and arteries participate in sympathetic hyperactivity in response to signals from the brain, further increasing systemic sympathetic tone (Dibona and Kopp, 1977). Sympathetic activation can initially be beneficial but eventually becomes maladaptive. In a state of sympathetic hyperactivity, a number of pathological events take place: abnormalities of hormonal secretion such as increased catecholamine, renine and angiotensin II levels, increased blood pressure due to peripheral vascular constriction and/or water and sodium retention, renal failure due to impaired glomerular filtration and nephron loss, cardiac dysfunction and heart failure due to left ventricular hypertrophy and myocyte loss, stroke, and even diabetes. Therefore, modulation (reduction/removal) of this increased sympathetic activity can slow or prevent the progression of these diseases. Recently, renal nerve denervation using high radio frequencies has become a recognized method to treat drug resistant hypertension (Esler et al., 2010 and Krum et al., 2009) and glucose metabolism abnormality (Mahfoud, 2011). However, certain methodologies by which renal nerve ablation or denervations are performed are either primitive, or are conducted in a manner whereby the medical professional operates with undue uncertainty respecting the location of the renal nerves critical in the disease pathway. The present invention seeks to rectify certain of these problems.

Renal Sympathetic Nerve Hyperactivity and Hypertension

Renal sympathetic nerve hyperactivity's contribution to the development and perpetuation of hypertension has been systematically investigated. This connection has been explored due in large part to the fact that, despite the availability of various pharmaceutical products and combination pharmaceutical products, and resources to assist patients' lifestyle changes, the rate of treatment of hypertension has remained surprisingly low. In particular, approximately ⅓ of hypertensive patients are not fully responsive to even optimized drug therapy and the measured blood pressure range amongst this cohort remains abnormal. This manifestation is called drug resistant hypertension. In approximately half of hypertensive patients, blood pressure remains higher than accepted treatment target levels. Amongst these patents with "essential" hypertension (i.e. persistent and pathological high blood pressure for which no specific cause can be found), it has been suggested that underlying pathophysiologies which are non-responsive to current treatment regimens exist. Further, it has been noted in such patients that efferent sympathetic renal nerve outflow stimulates renin release, increases tubular sodium reabsorption, and reduces renal blood flow, while afferent nerve signals from the kidney modulate central sympathetic outflow and thereby contribute to regulation of sodium and water metabolism, vascular tone/resistance and blood pressure.

Various data have confirmed the positive effects of renal nerve blocking on decreasing hypertension; data have further confirmed the connection between increased sympathetic nervous system activity and hypertension. In particular, studies have shown renal dysfunction as a mechanism of increased sympathetic nervous system activity leading to hypertension (Campese, 2002; Ye, 2002), that blocking renal nerve activity controls hypertension in animals with chronic renal insufficiency (Campese, 1995), and that surgical renal denervation performed to eliminate intractable pain in patients with polycystic kidney disease also eliminates hypertension (Valente 2001). Additional studies have identified increased noradrenaline spillover into the renal vein as the culprit in essential hypertension (Esler et al., 1990), and have shown that denervation by nephrectomy eliminates hypertension in humans on dialysis with severe hypertension refractory to multi-drug therapy (Converse 1992). Renal denervation has also been shown to delay or prevent the development of many experimental forms of hypertension in animals (e.g. spontaneously hypertensive rats (SHR), stroke prone SHR, New Zealand SHR, borderline hypertensive rats (BHR), Goldblatt 1K, 1C (rat), Goldblatt 2K, 2C (rat), aortic coarctation (dogs), aortic nerve transection (rat), DOCA-NaCL (rat, pig), Angiotensin II (rat, rabbit), fat feeding—obesity (dog), renal wrap (rat)XDiBona and Kopp, 1997).

Renal Sympathetic Nerve Hyperactivity, Insulin Sensitivity and Glucose Metabolism Renal nerve hyperactivity is also posited to play a role in insulin sensitivity and glucose metabolism. Specifically, an increase in noradrenaline release accompanying renal nerve hyperactivity results in reduced blood flow, which in turn is associated with reduced glucose uptake. This indicates an impaired ability of cells to transport glucose across their membranes. Renal nerve hyperactivity is related to a neurally mediated reduction in the number of open capillaries, so that there is an increased distance that insulin must travel to reach the cell membrane from the intravascular compartment. Insulin-mediated increases in muscle perfusion are reduced by approximately 30% in insulin-resistant states. Consequently there is a direct relationship between muscle sympathetic nerve activity and insulin resistance, and an inverse relationship between insulin resistance and the number of open capillaries. (Mahfoud, et al., 2011). Renal sympathetic nerve hyperactivity is thus associated with certain aspects of diabetes mellitus and/or metabolic syndrome; sympathetic hyperactivity induces insulin resistance and hyperinsulinemia, which in turn produces additional sympathetic activation. Studies have been performed evaluating the effects of renal denervation on diabetic criteria.

A study by Mahfoud et al. (2011) tested the effect of renal denervation on patients who had type 2 diabetes mellitus, as well as high blood pressure of ≥160 mm Hg (or ≥150 mm Hg for patients with type 2 diabetes mellitus) despite being treated with at least 3 anti-hypertensive drugs (including 1 diuretic). At baseline and at follow-up visits taking place at one (1) and three (3) months after the procedure, blood chemistry, and fasting glucose, insulin, C peptide, and HbA1c were measured, while an oral glucose tolerance test (OGTT) was performed at baseline and after 3 months. Three months after denervation, diabetic indicators had substantially improved. Insulin sensitivity increased significantly after renal denervation. After the procedure, 7 of 25 patients showed improvement in OGTT. The Mahfoud et al. study thus conclusively demonstrated that the renal sympathetic nervous system is an important regulator of insulin resistance and shows that renal nerve ablation substantially improves insulin sensitivity and glucose metabolism. During 1950s, surgical sympathectomy was utilized in humans as a treatment for severe hypertension before the availability of antihypertensive medicine (Smithwick and Thompson, 1953). However, such surgical renal denervation was extremely invasive and involved a major surgical procedure; therefore, it had great limitations in clinical practice (DiBona, 2003).

Recently, endovascular catheter technologies have been preferably utilized to create selective denervation in the human kidney. The renal nerves primarily lay outside the vessel tunica media, within the renal artery adventitial space. Consequently, radiofrequency energy, laser energy, high intensive focused ultrasound and alcohol can be delivered to renal artery walls, and cryoablative techniques likewise utilized on renal artery walls, via the renal artery lumen, to ablate sympathetic renal nerves. The first human study of renal nerve ablation by catheter methodologies took place on hypertensive patient test subjects in 2009. Patient test subjects were enrolled whose standing blood pressure (SBP) was more than or equal to 160 mmHg despite the patient being on more than three anti-hypertensive medications (including diuretics), or who had a confirmed intolerance to anti-hypertensive medications (Krum et al., 2009). In this study of forty-five (45) patients overall baseline patient blood pressure consisted of (mmHg) of 177/101±20/15.

In order to assess whether renal denervation was effectively performed, after renal nerve ablation, renal noradrenaline spillover was measured to determine the success of the sympathetic denervation. Blood pressure was measured at baseline, and at 1 month, 3 months, 6 months, 9 months, and 12 months after the procedure. At each time point, decreases in both systolic and diastolic pressure were registered, with decreases continuing with the passage of time. Post-procedure, an overall decrease in total body noradrenaline spillover of 28% (p=0.043) was shown amongst the 45 test subjects, of which approximately one third was attributable to the renal sympathetic denervation.

Current Protocols in Renal Denervation

After the Krum et al. study, there have been established certain accepted methodologies for performing renal nerve ablation through catheter means, though said methodologies comprise some variation. Typically, renal nerve ablation comprises catheter-based methods in which a patient is administered four (4) to six (6) two-minute radio frequency (RF) treatments per renal artery, with the radio frequency being generated by a radio frequency (RF) generator, which is automated, low-power, and has built-in safety algorithms. The radio frequencies, usually of 5-8 watts, are administered by catheter in the renal artery through movement of the catheter distal to the aorta to proximal to the aorta with application of the radio frequencies in spaced increments of 5 mm or more.

In the aforementioned Mahfoud et al. diabetes study, the following specific ablation protocol was followed: a treatment catheter was introduced into each renal artery by use of a renal double curve or left internal mammary artery guiding catheter, radiofrequency ablations lasting up to 2 minutes each were applied with low power of 8 watts to obtain up to 6 ablations separated both longitudinally and rotationally within each renal artery. Treatments were delivered from the first distal main renal artery bifurcation to the ostium. Catheter tip impedance and temperature were constantly monitored, and radiofrequency energy delivery was regulated according to a predetermined algorithm.

Functionally, the optimized goal of ablation of the renal arteries is to selectively disable the renal sympathetic (both afferent and efferent) nerves without impairing sympathetic signaling to other organs, and to precisely deliver energies to the locations in which renal sympathetic nerves are distributed in order to denervate the nerves. At present, renal nerve ablation is done in a "blind" fashion—that is, before the ablation radiofrequency is delivered, the physician who performs the procedure does not know where the renal sympathetic nerves are distributed so that the whole length of renal artery is ablated; furthermore, whether renal nerves have really been ablated or not can only be confirmed by measuring a secondary effect—i.e. norepinephreine spillover, after completion of the procedure. At present, approximately 89% of patients respond to renal denervation treatment in a small and very selective patient population (Krum et al., 2009 and Esler et al. 2010). However, recent data showed that the responder rate can be as low as less than 50% among treated patients (Medical devices: pg 1-2, Feb. 22, 2012). In some cases, treatment failures may be due to regeneration of renal nerves (Esler et al., Lancet 2010, p. 1908), while in others, treatment failures may be due to failure to correctly target and sufficiently complete ablation of the renal nerves. Therefore, methods to precisely detect where renal nerve distribution occurs along the renal arteries, so that ablation targets can be provide to physicians, and to monitor clinically relevant indices (such as blood pressure, heart rate and muscle sympathetic nerve activity) to assess whether efficient ablations are delivered, are urgently needed. As above discussed, renal afferent and efferent nerve system serves as a common pathway for sympathetic hyperactivity, therefore stimulation of renal nerve can cause increases in blood pressure and changes in heart rate. Changes in heart rate can be either increased due to direct stimulation of sympathetic nerves, or decreased blood pressure due to an indirect reflex regulation via baroreflex.

An improved methodology would involve a renal nerve mapping approach by which individual segments of the renal artery are stimulated by a low power electrical current while blood pressure, heart rate and muscle sympathetic nerve activity were measured. If measurable changes in blood pressure, heart rate and muscle sympathetic nerve activity are detected, such as increases in blood pressure or changes in heart rate or decreases in muscle sympathetic nerve activity, there is a reasonable expectation that ablation at that site should be performed so as to destroy nerve fibers in more precise way, and consequently, improve the clinical measures desired. These improved renal nerve mapping and catheterization technologies would seek to minimize unnecessary ablation in the types of denervation procedures described, guide operators to perform renal ablation procedures, and to optimize clinical outcomes of renal nerve ablation for treatment of hypertension, heart failure, renal failure and diabetes.

Anatomical Mapping and Targeting in Renal Nerve Ablation

Anatomically, the nerves carrying fibers running to or from the kidney are derived from the celiac plexus (a/k/a the solar plexus) and its subdivisions, lumbar splanchic nerves, and the intermesenteric plexus (DiBona and Kopp, 1997, p. 79). The celiac plexus consists of the suprarenal ganglion (i.e. the aorticorenal ganglion), the celiac ganglion, and the major splanchnic nerves. The celiac ganglion receives contributions from the thoracic sympathetic trunk (thoracic splanchnic nerves), and the vagus nerves (DiBona and Kopp, 1997, p. 79).

The suprarenal ganglion gives off many branches toward the adrenal gland, some of which course along the adrenal artery to the perivascular neural bundles around the renal artery entering the renal hilus; other branches enter the kidney outside the renal hilar region. The major splanchic nerve en route to the celiac ganglion gives off branches to the kidney at a point beyond the suprarenal ganglion. The celiac ganglion gives off branches to the kidney that run in the perivascular neural bundles around the renal artery entering the renal hilus (DiBona and Kopp, 1997, p. 79).

The lumbar and thoracic splanchnic nerves are derived from the thoracic and lumbar paravertebral sympathetic trunk, respectively. They provide renal innervation via branches that go to the celiac ganglion but also via branches that go to the perivascular neural bundles around the renal artery entering the renal hilus (DiBona and Kopp, 1997, p. 79).

The intermesenteric plexus, containing the superior mesenteric ganglion, receives contributions from the lumbar splanchnic nerves and gives off branches that often accompany the ovarian or testicular artery before reaching the kidney (DiBona and Kopp, 1997, p. 79). The renal nerves enter the hilus of the kidney in association with the renal artery and vein (DiBona and Kopp, 1997, p. 81). They are subsequently distributed along the renal arterial vascular segments in the renal cortex and outer medulla, including the interlobar, arcuate, and interlobular arteries and the afferent and efferent glomerular arterioles (DiBona and Kopp, 1997, p. 81).

While the renal nerve architecture is of paramount consideration before ablation can take place, individual renal architecture must be carefully considered before catheterization for denervation can be contemplated. As noted with respect to the Krum et al./Esler et al. studies, eligibility for catheterization was determined in part by an assessment of renal artery anatomy, renal artery stenosis, prior renal stenting or angioplasty, and dual renal arteries. Not only is aberrant or unusual renal architecture an impediment to catheterization in and of itself, but normal variation in renal architecture may prove challenging, especially when an off-label catheter system (i.e. a catheter not specifically designed for renal artery ablation per se) is used. The risks of renal catheterization with sub-optimal catheter systems may include the rupture of renal arteries due to coarse or jagged manipulation of such catheter tips through delicate tissue, rupture of and/or damage to the artery wall or renal artery endothelium due to excessive ablation energy applied, and dissection of the artery. Therefore, catheter systems specially designed for renal architecture and common aberrations in renal architecture are desirable, in order that a large spectrum of the eligible refractory patient population be treated.

Catheter Systems

Certain catheter systems designed for coronary artery systems are similar to those which may be used in renal nerve ablation; in particular, ablative catheter systems designed for coronary artery use which are tailored to remedy tachycardia may be used for renal nerve ablation procedures. As such, these systems typically contain electrodes which are designed to assess the pre-existing electric current in the cardiac tissue through which the catheter electrodes are being passed. In contrast, ideal catheter systems for renal denervation would optimally be engineered with dual functions: to map renal nerve distribution and stimulate renal nerve activity by providing electrical stimulation so that a physician operator may assess in real-time patient physiological changes occurring as a result of said electrical stimulation and renal denervation. However, such catheters have not previously been developed.

Known catheter systems often possess multiple functionalities for cardiac uses. Certain notable catheter systems on the market include the following:

Ardian Symplicity® Catheter System

The current catheter system utilized for renal ablation, comprising both an ablation catheter and radio frequency generator, i.e. the Symplicity® Catheter System, is specially designed by Ardian Inc. (Mountain View, Calif., USA). However, the Symplicity® catheter does not possess mapping functions and ablation is its only function; and secondly, such catheter systems (as well as angioplasty and distal protection devices for angioplasty) were designed for coronary and carotid artery systems—hence, these systems would be used "off-label" for renal nerve ablation and denervation to treat hypertension, heart failure, renal failure and diabetes.

The fact that some cases of hypertension are resistant to treatment by pure pharmacological means has reignited the use of invasive techniques in treating these cases. Historically, surgical renal denervation was the prominent treatment for severe cases of hypertension prior to the introduction of orally administered anti-hypertensive drugs (Smithwick and Thompson, 1953). This type of conventional surgery was, however, extremely invasive and involved a major surgical procedure which greatly limits it practicality (DiBona, 2003). At least two clinical studies have, to a certain extent, provided support to the use of minimally invasive catheter-based radiofrequency (RF) renal nerve ablation in the treatment of resistant hypertension (Krum et al., 2009; Esler et al., 2009). Patients with hypertension resistant to the available anti-hypertensive drugs were selected for these studies and this interventional procedure demonstrated a 89% clinical success rate in lowering their blood pressure in a small and very selective patient population.

While there is growing interest in using such minimal invasive interventional techniques for treatment of hypertension, all systems on the market, including the Ardian Symplicity® Catheter System, are not optimally designed for this purpose. There are apparent shortcomings, even in the Ardian Symplicity® Catheter System, that limit the certainty of the interventional outcome.

An important aspect not considered in the current interventional systems and techniques, is the precision and accuracy in locating and delivering an effective dose of energy to a suitable ablation spot in the arterial wall. The current commonly accepted procedures for performing renal nerve ablation via catheters typically consists the steps of administering to the arterial wall 4 to 6 ablations, each made by 2 minutes of RF energies and spaced both longitudinally and rotationally along the inner wall of each renal artery. The ablations had to be delivered "blindly" in this helical manner because the exact location of the nerves innervating the renal artery with respect to the ablation catheter is unknown before and during the delivery of the ablation energy. An inaccurately directed dose of energy not only causes unnecessary damage to healthy tissues and non-sympathetic nerves but more importantly could not provide the promised solution for hypertension which the interventional procedure was intended for. In fact, in certain clinical settings other than the two published studies, the responder rate of the current "blind" type of interventional procedure could go as low as 50% (Medical devices: pg 1-2, Feb. 22, 2012).

Theoretically, precise nerve ablation in the wall of an artery could be achieved by mapping the location of the nerves innervating the arterial wall prior to delivery of the dose of energy. By monitoring physiological parameters associated with the autonomic nervous systems such as the blood pressure, heart rate and muscle activity while a stimulus is delivered to a selected location on the arterial wall, the presence of autonomic nerves in the immediate vicinity of this location will be reflected from the changes in the monitored physiological parameters (Wang, US 2011/0306851 A1).

Further, the sympathetic and parasympathetic nerves of the autonomic nervous system often exert opposite effects in the human body including their control on blood pressure and heart rate. While ablation of the sympathetic nerves innervating the arterial walls will relieve hypertension, there is an equally possible chance that other tissues such as parasympathetic nerves are ablated in the "blind" type of interventional procedure. The result for decreasing or removal of nerve activity blindly may worsen the hypertension as could be inferred from several animal studies (Ueda et al., 1967; Beacham and Kunze, 1969; Aars and Akre, 1970; Ma and Ho, 1990; Lu et al. 1995).

The cause of failure in the current treatment was attributed to regeneration of the nerves after the ablation (Esler et al., 2010) and may also be related to both the inability to deliver the dose of energy to the targeted nerve and an insufficient dose of energy delivered for effective ablation. At present, the success of renal denervation is only assessed by the measurement of a secondary effect known as norepinephrine spillover at least days after the interventional procedure (Krum et al., 2009) and lack a method for immediate post-procedural assessment. In order to improve the success rate of the interventional procedure, it is important to not only locate suitable ablation spots on the arterial wall, but also ensure that the energy is precisely and accurately delivered to a targeted nerve during the ablation process, and confirm immediately after the ablation that the dosage of energy delivered has effectively ablated the targeted nerve.

In response to the shortcomings of the current system and methods for nerve ablation, the present invention introduces improvements by providing a system and methods for accurate and precise location of suitable ablation spots on a renal arterial wall; ensuring sufficient ablation energy is accurately directed into a targeted nerve and to conduct immediate post-procedural assessment of nerve ablation. A catheter system optimal for renal nerve mapping is also provided by this invention.

SUMMARY OF THE INVENTION

It was with the preceding needs in mind that the present invention was developed. Embodiments of the disclosure are directed to system and method for accurate and precise location of areas innervated with nerves on an arterial wall; ensuring sufficient energy is accurately directed into a targeted nerve to elicit a desired response such as stimulation and ablation; and to conduct immediate post-procedural assessment of a sufficient nerve ablation. Further, the embodiments of the disclosure are also directed to provide an interface for clear representation of the location and type of nerves that are innervating the location being probed on the arterial wall.

The present invention provides a method for identifying the presence of functional sympathetic and parasympathetic nerves innervating the arterial walls in a human body with respect to the location of a dose of energy. The method comprises one or more of the steps of preparing a baseline of one or more of physiological parameters prior to the delivery of a dose of energy to the arterial wall; delivering a dose of energy to the arterial wall; detecting the physiological changes as a result of the delivered energy; rating the change based on a set of empirically pre-determined values; and determining if the area where the energy was delivered lies in the vicinity of functioning sympathetic or parasympathetic nerves based on the ratings.

In one embodiment, said method is used for locating suitable nerve ablation sites relevant to baroreflex including both sympathetic and parasympathetic systems in arterial walls prior to a nerve ablation procedure. In certain embodiments, the nerve ablation procedure is for denervation of the renal artery. In another embodiment, the method is used for ensuring the accurate delivery of ablation energy to a targeted nerve in the arterial wall during a nerve ablation process. In a further embodiment, the method is used for immediate post-procedural assessment of the nerve ablation process to ensure that the targeted nerve has been ablated by the energy delivered in a nerve ablation procedure.

In certain embodiments, the energy is delivered to the arterial wall at dosage suitable for nerve stimulation. In other embodiments, the energy is delivered to the arterial wall at a dosage suitable for nerve ablation.

In one embodiment, the physiological parameters comprise blood pressure, heart rate, biochemical levels, cardiac electrical activity, muscle activity, skeletal nerve activity, action potential of cells or other measurable reactions as a result of these physiological changes such as pupil response, electromyogram and vascular constriction.

In some embodiments, an area on the arterial wall that, upon stimulation, causes increase in blood pressure and heart rate is considered as innervated with sympathetic nerves while, in contrary, an area on the arterial wall that, upon stimulation, causes decrease in blood pressure and heart rate is considered as innervated with parasympathetic nerves.

In an embodiment, the energy for ablation is considered to be delivered accurately to a targeted nerve innervating the arterial wall when the physiological parameters deviate significantly from the baseline during the ablation process.

In one embodiment, the nerve ablation procedure is considered to be successful when an area, confirmed to be innervated with nerves with said method before the delivery of ablation energy, no longer leads to changes in the physiological parameters such as blood pressure and heart rate when stimulation energy is delivered to this spot.

The present invention also provides a system for locating and identifying nerves innervating an arterial wall. The system comprises one or more devices capable of delivering a dose of energy to an arterial wall; one or more sensors to receive signals of physiological parameters; one or more devices for analysis of signals from the sensors; and one or more indicators or panels capable of displaying the results of the analysis In one embodiment, the dose of energy delivered by the energy delivery device can be controlled to achieve either nerve stimulation or nerve ablation. In another embodiment, two separate devices are used to carry out nerve stimulation and nerve ablation independently.

In another embodiment, the energy delivered is one or more of electrical, mechanical, ultrasonic, radiation, optical and thermal energies.

In some embodiments, said sensors detect physiological parameters which comprise blood pressure, heart rate, biochemical levels, cardiac electrical activity, muscle activity, skeletal nerve activity, action potential of cells and other measurable reactions as a result of the above such as pupil response, electromyogram and vascular constriction. In certain embodiments, the signals corresponding to the physiological parameters are detected with commercially available technologies known in the field.

In another embodiment, the device for digital analysis of the physiological signals is a microcontroller or computer.

In one embodiment, the analyzed results are displayed using different colored indicators. An area innervated with sympathetic nerves is represented with a green indicator and an area innervated with parasympathetic nerves is represented with a red indicator. In another embodiment, the analyzed data are displayed on a digital viewing panel.

In one embodiment, the set of indicators or panels may be built into devices in the system such as the energy delivery device. In certain embodiments, the set of indicators or panels may exist as a separate entity in the system.

The present invention also provides for specially-designed catheters with a distal end (i.e. the catheter tip) in shapes customized to renal architecture, possessing one or more electrodes to map renal nerve distribution, to perform renal ablations, to perform post-ablation assessment and to perform angiography. In certain embodiments, the electrodes of such catheters are sequentially spaced along the length of the catheter tip, where the electrode faces make contact with segmented portions of the renal artery lumen. In certain embodiments, the tip of the catheter is steerable and has a single electrode for emitting radio frequency energy. In certain embodiments, the shape of the catheter tip is a single helix wherein the coil of the helix is either round or flat in shape. In other embodiments, the catheter tip is a double helix wherein the coils of the helices are either round or flat in shape. In further embodiments, the catheter tip may comprise a balloon around which is wrapped a helical coil, wherein spaced along the length of the helical coil are electrodes; alternately, the catheter tip may comprise a balloon around which is an umbrella component encapsulating the balloon, and wherein spaced along the umbrella component are electrodes. In variations of both embodiments, the coil or umbrella component may be either round or flat in shape; consequently the electrodes spaced along the length of the coil or umbrella may be round or flat in shape, depending upon the underlying shape of the coil or umbrella.

In further embodiments, the catheter tip may comprise an umbrella shape or frame with a closed end, or umbrella with an open end.

In certain embodiments, the above catheter tips may be introduced into the arterial architecture to perform the functions of a stent.

In one embodiment, the diameter of these catheter tips may vary from 0.5 mm to 10 mm; the length of the catheter tips may vary from 20 mm to 80 mm; the diameters of coil may vary from 3.0 mm to 7.5 mm; the distances between each coil may vary from 4 mm to 6 mm; and the fully uncoiled lengths of the coils may vary from 31 mm to 471 mm.

The electrodes of the catheters may be activated independently of one another or can be activated in any combination to emit electrical stimulation or radiofrequency energy. The electrodes each have dual functions of delivering electrical stimulation or radiofrequency energy. Electrical stimulation is used to identify and map segments of renal artery lumen beneath which lie renal nerves of importance. Said identification and mapping is accomplished through the monitoring of a physiological response or responses to the applied electrical stimulation, such as changes in blood pressure response and heart rate or muscle sympathetic nerve activity (Schlaich et al., NEJM 2009), or renal norepinephrine spillover (Esler et al. 2009, and Schlaich et al., J Htn. 2009), wherein changes in physiological response indicate the presence of an underlying sympathetic nerve distribution in the vicinity of the activated electrode. In another embodiment, individual electrodes of the catheters may be activated in physician operator-selected combinations in order to assess maximal physiological response, and the consequent locations of underlying renal nerves. The electrodes of the catheters are able to emit not just electrical current of sufficient strength to stimulate renal nerve, but thermal energy such as radiofrequency energy to ablate underlying renal nerve tissue based on renal nerve mapping results. In other embodiments, separate electrodes of the catheters can be selectively activated to emit ablative energy such as high radiofrequency energy wherein the choice of the activated electrodes is based upon the results of the mapping of the nerves. In further embodiments, based on the mapping of the renal nerves, ablative techniques using other types of ablative energy such as laser energy, high intensive focused ultrasound or cryoablative techniques can be utilized on renal artery walls to ablate the sympathetic renal nerves.

In certain embodiments, these catheters are interchangeably used with existing radiofrequency generators which are presently utilized with existing cardiac catheter systems.

In one embodiment, the aforementioned catheter systems may be utilized with any variety of acceptable catheter guidewire previously inserted into the patient's body to guide the catheter tip to the desired location. They may also be used with devices and other instruments that may be used to facilitate the passage of like devices within the cardiovascular and renal vascular systems, such as sheaths and dilators. When required, the aforementioned catheter systems may also be utilized with a puller wire to position the catheter tip.

The present invention also provides methods of using the catheters described herein to map renal nerve distribution, comprising the steps of using electrical stimulation while monitoring changes in physiological responses, such as blood pressure and heart rate, to map renal nerve distribution and identify ablation spots within renal arteries for ideal denervation of renal nerves. These methods comprise activating the independent electrodes of the described catheters to emit an electrical charge to stimulate the underlying renal nerve while monitoring physiological responses such as blood pressure and heart rate; the presence of changes in physiological response indicate the presence of an underlying sympathetic nerve in the vicinity of the activated electrode and a superior location for ablation. An agglomeration of mapping data may take the form of a clinically useful guide respecting renal nerve distribution to assist clinicians in performing ablation.

DETAILED DESCRIPTION OF THE INVENTION

Please note that as referred to throughout this specification, the term "catheter" references the entire length of a catheter apparatus, from the distal portion intended for introduction into the desired target anatomy for ablation or other action, extending through to the juncture where the catheter meets the cable linking the catheter to an RF generator. As referenced to through this specification, the term "catheter tip" is used to reference the distal portion of the catheter which carries electrodes, and performs stimulative, ablative, and mapping functions within the body at a targeted site of action. The term "catheter tip" is used interchangeably with terms referencing the "distal portion" of any recited catheter.

The renal nerve architecture is of paramount consideration before successful ablation can take place; therefore, individual renal nerve architecture must be carefully considered or mapped before catheterization for denervation can be successfully accomplished. The presence of aberrant or unusual renal architecture, as well as normal variation in renal nerve architecture among individuals require mapping of the renal nerves before ablation. In other words, mapping of the renal nerves is required before catheter denervation because the best spots for ablation are "random" in the sense that the best spots for ablation vary from one person to another, and from one artery to another. Optimal ablation thus requires identification or mapping of renal nerves prior to catheter ablation.

This invention provides a system and method for locating sites innervated with functional nerves in the wall of arteries, particularly the renal artery, though persons skilled in the art will appreciate that nerves innervating other arteries or vessels in the human body may be located using this invention. The system comprises one or more devices capable of delivering a dose of energy to the wall of an artery; one or more sensors to receive inputs of physiological signals; one or more devices for analysis of signals from the sensors; and one or more indicators or panels capable of displaying the results of the analysis.

Figure 1:
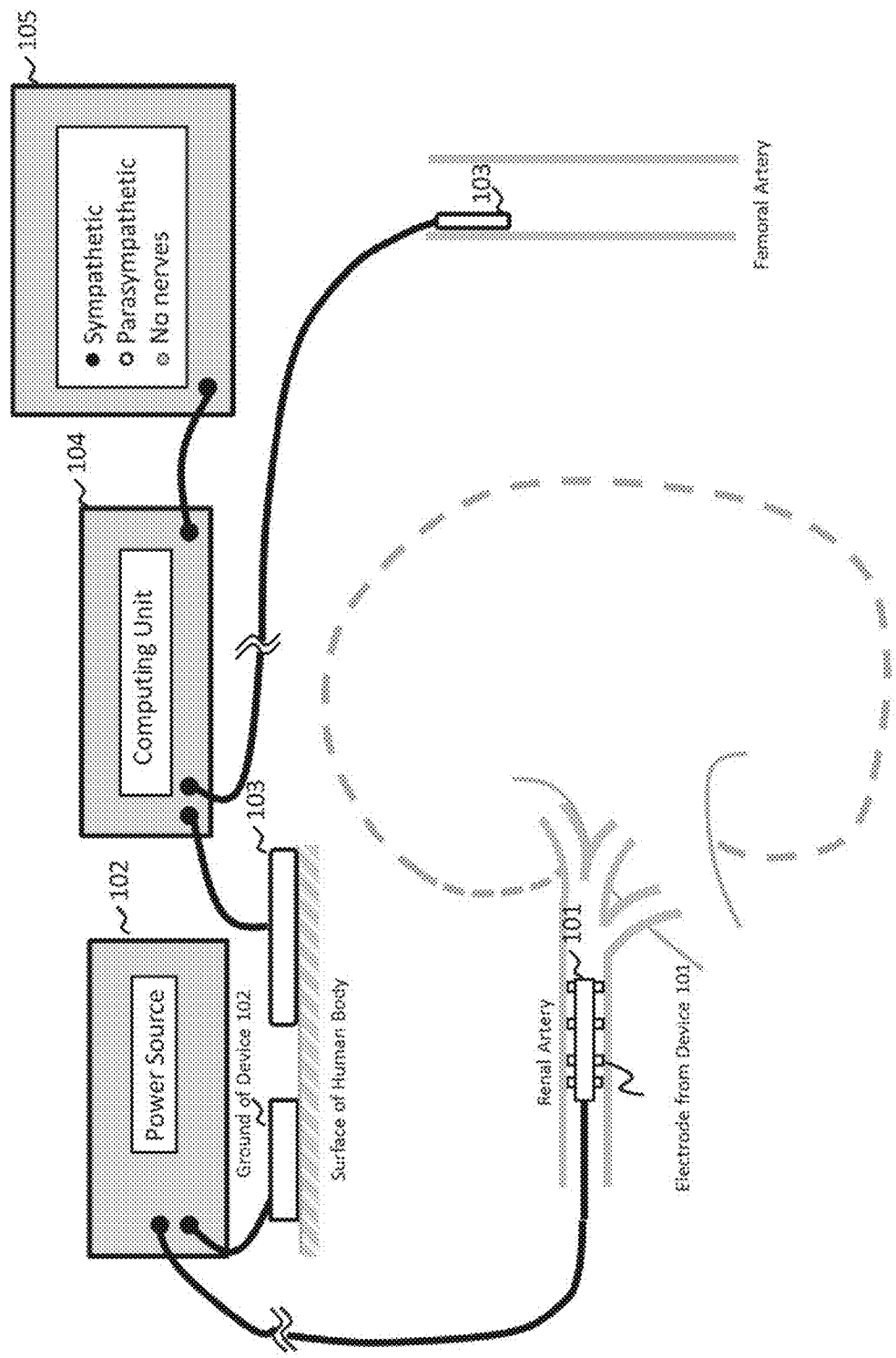
FIG. 1 is a schematic of a system of the present invention for locating and identifying functional nerves innervating the wall of an artery. The system comprises device 101 for delivery of energy to the arterial wall; power source 102 for powering device 101; sensor 103 for detecting signals of physiological parameters; device 104 for analyzing the data from sensor 103; and indicator 105 to display the results from device 104.

FIG. 1 depicts an exemplary system in accordance with an aspect of the invention, namely a renal denervation system using blood pressure and heart rate as the physiological parameters for identifying nerve response. The system comprises one or more of devices 101 for delivery of energy to the arterial wall which is in electrical communication with a power source 102. System further comprises sensors 103 for detecting physiological signals in electrical communication with device 104 for analysis of the physiological signals. The indicator 105 in electrical communication with device 104 displays the result of the analysis from device 104. Device 101, in the form of a dual-function catheter, is shown inserted into the renal artery via minimal invasive interventional procedure in this embodiment. At least one of the electrodes of device 101 contacts the renal arterial wall at a defined location and is capable of delivering a dose of energy from the power source 102 for stimulation or ablation of the nerves that may be innervating the area of the arterial wall for which the electrode is in contact with. Sensors 103 detect changes in blood pressure and/or heart rate as energy sufficient for nerve stimulation or ablation is delivered from an electrode on device 101 to the spot the electrode is contacting on the arterial wall. The signals from sensor 103 will be inputted to device 104 which will determine digitally whether the signal elicited is due to sympathetic or parasympathetic nerves, or the lack thereof. Indicator 105 will then display the result of the analysis from device 104.

In one embodiment of the invention, device 101 is an invasive device inserted into an artery capable of delivering energy to a nerve innervating the artery, resulting in nerve stimulation or ablation. In another embodiment, device 101 is made up of two separate entities, one delivering the energy for nerve stimulation, and the other nerve ablation. In a different embodiment, device 101 is a single-electrode catheter or multi-electrode catheter.

In one embodiment, power source 102 delivers energy to the arterial wall via device 101. In another embodiment, energy is delivered remotely through the human body by power source 102 into the arterial wall without device 101. In a further embodiment, power source 102 is a multi-channel power source capable of delivering separate doses of energy independently to distinct locations on the arterial wall. In other embodiments, power source 102 is a single channel power source capable of delivering only 1 dose of energy each time. In another embodiment, the dosage of energy to be delivered by power source 102 is adjustable to induce different effects on a targeted nerve such as stimulation or ablation. In further embodiments, the energy delivered by power source 102 is one or more of electrical, mechanical, ultrasonic, radiation, optical and thermal energies.

In one embodiment, sensors 103 detect signals from physiological parameters comprising blood pressure, heart rate, biochemical levels, cardiac electrical activity, muscle activity, skeletal nerve activity, action potential of cells and other measurable reactions as a result of the above such as pupil response, electromyogram and vascular constriction. In a further embodiment, sensors 103 detect said signals externally with or without contacting any part of the human body. In another embodiment, sensors 103 detect said signals inside the human body by placing into contact with, or in the vicinity of, the lumen of interest such as the renal artery or femoral artery or any other artery. In yet another embodiment, sensor 103 could be a sensor from part of another equipment that is used in conjunction with this invention during the interventional procedure.

In an embodiment, device 104 is one or more microcontrollers or computers capable of digital analysis of the signals arising directly or indirectly from sensor 103.

In one embodiment, indicator 105 is one or more digital viewing panels that display the result from the analysis of device 104. In another embodiment, one or more results of said analysis from multiple locations on the arterial wall are simultaneously displayed on indicator 105. In a further embodiment, indicator 105 also displays one or more the physiological signals from sensor 103; energy related information from power source 102 such as current, frequency, voltage; tissue-electrode interface related information such as impedance; and information related to device 101 such as temperature. In certain embodiments, indicator 105 comprises a set of different colored lights each distinctly representing sympathetic nerve, parasympathetic nerve or no nerve. In other embodiments, indicator 105 represents the result from analysis of device 104 with texts, symbols, colors, sound or a combination of the above.

In certain embodiments, device 4 and indicator 5 are integrated as a single device and, in further embodiments, both device 4 and indicator 5 are integrated into power source 2.

In yet another embodiment, sensor 103, device 104 and indicator 105 exist independently from device 101 and power source 102 such that sensor 103, device 104 and indicator 105 can be used with other external or invasive methods for energy delivery into the vessel wall such as high-intensity focused ultrasound.

The present invention additionally provides a method for identifying the presence of functional sympathetic or parasympathetic nerves innervating a selected area on the arterial wall based on changes in physiological parameters induced by a dose of energy. The method comprises one or more of the steps of preparing a baseline of the physiological parameters to be measured prior to the delivery of a dose of energy to the arterial wall; delivering a dose of energy to the arterial wall; detecting the physiological changes as a result of the delivered energy; rating the change based on a set of empirically pre-determined values; and, based on the ratings, determining if there are functional sympathetic or parasympathetic nerves in the vicinity of the site of energy delivery.

Figure 2:
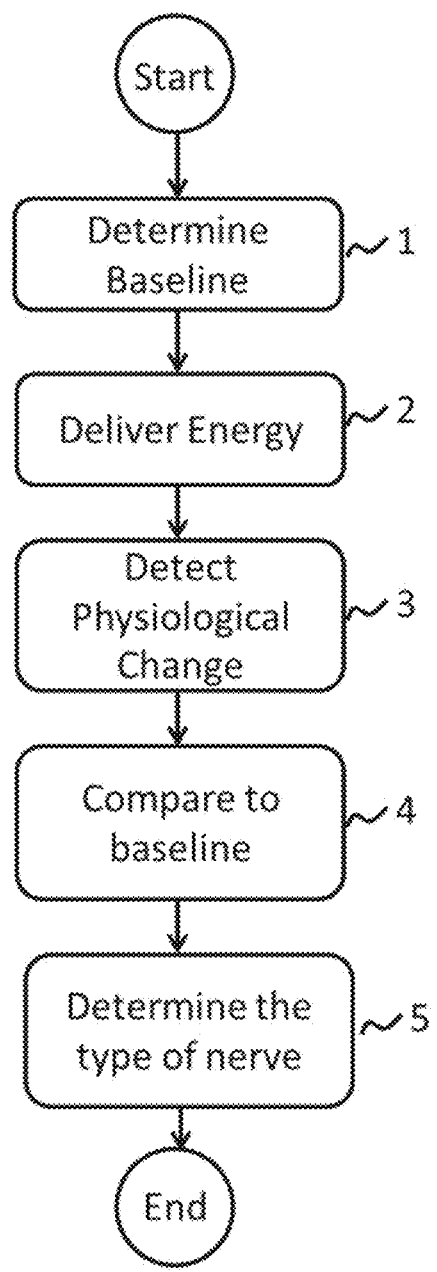
FIG. 2 is a schematic diagram depicting the steps in an embodiment of the method to determine whether functioning sympathetic or parasympathetic nerves are in the vicinity of a dose of energy delivered to the arterial wall. The graphs illustrate possible recorded physiological signals.
Figure 2:
Figure 2:
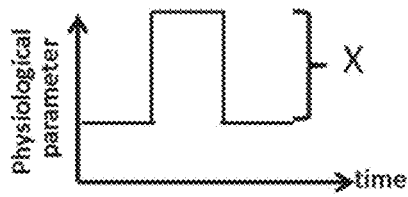
Figure 3A:
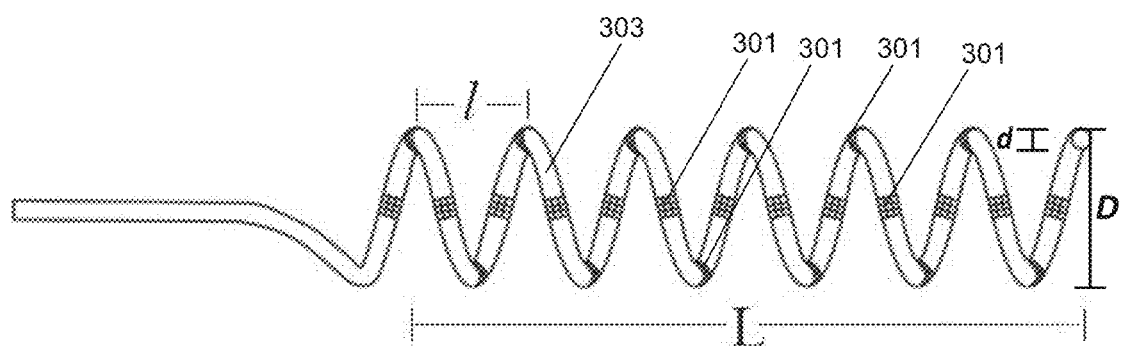
FIG. 3A shows an elevational view of the distal portion (catheter tip) of a single helix ablation catheter according to one embodiment of the present invention wherein electrodes 301 are placed at 90° intervals along the helix length, wherein the helical coil 303 itself is round, and wherein "L" designates the length of the distal portion, "l" designates the length of one turn of a single coil, "d" designates diameter of catheter tip and "D" designates diameter of the helical coil.
Figure 3B:
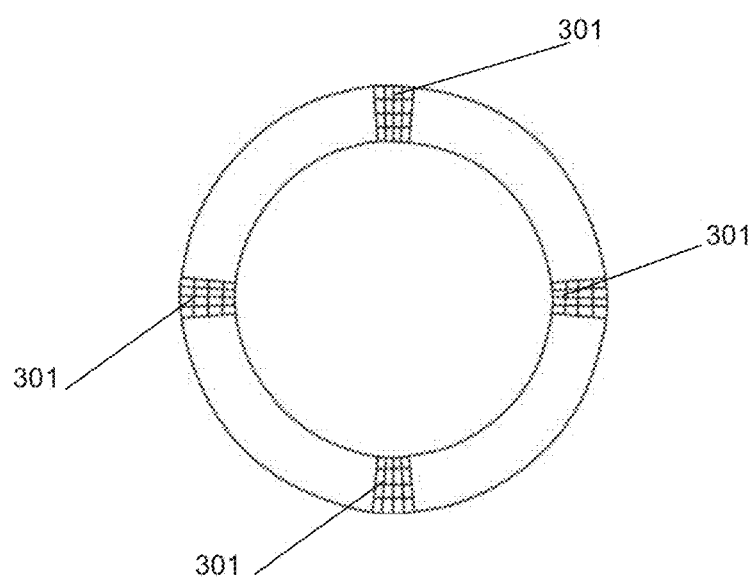
FIG. 3B shows the distribution of electrodes 301 in a single complete coil in the helix of the ablation catheter shown in FIG. 3A.
Figure 3C:
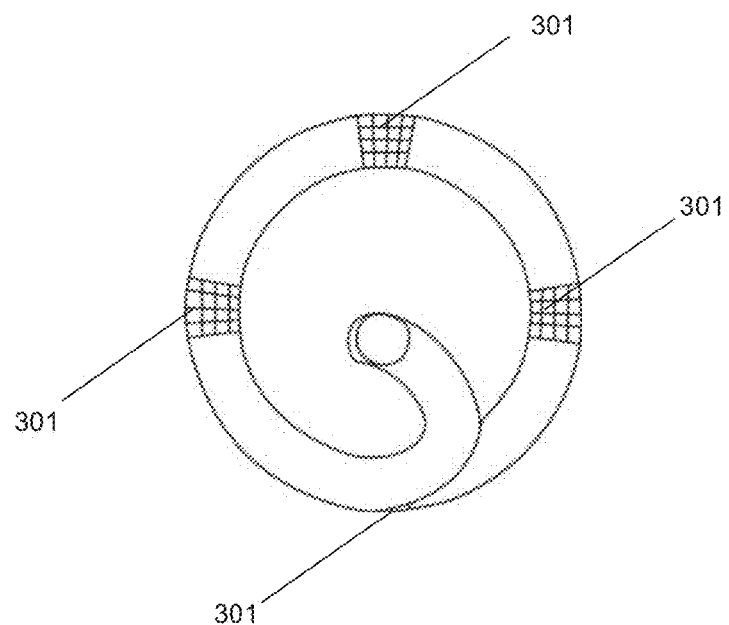
FIG. 3C shows an end-on view of the distal portion of a single helix ablation catheter according to the embodiment shown in FIG. 3A from the delivery direction of the lead, displaying only the first turn of the coil with electrodes 301.
Figure 3D:
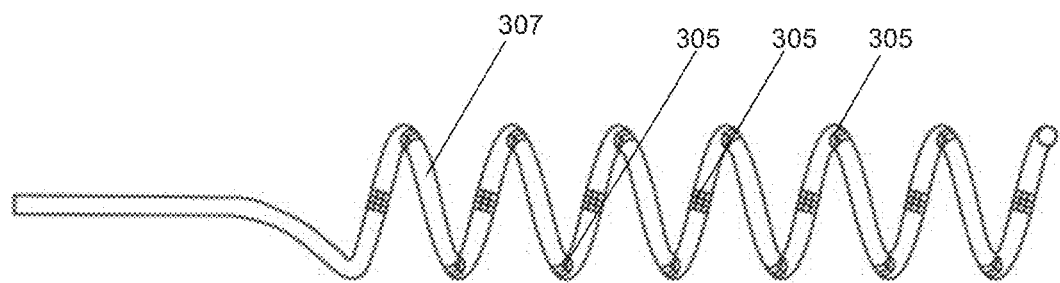
FIG. 3D shows an elevational view of the distal portion of a single helix ablation catheter according to an embodiment of the present invention wherein electrodes 305 are placed at 120° intervals along the helix length, and wherein the helical coil 307 itself is round.
Figure 3E:
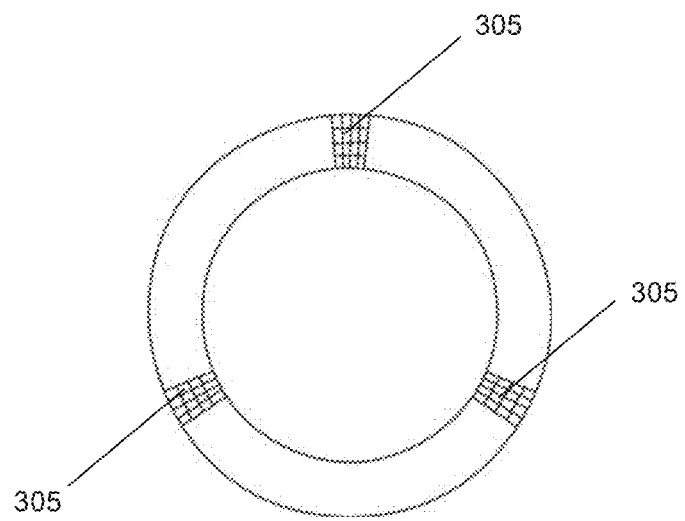
FIG. 3E shows the distribution of electrodes 305 in a single complete coil in the helix of the ablation catheter shown in FIG. 3D.
Figure 3F:
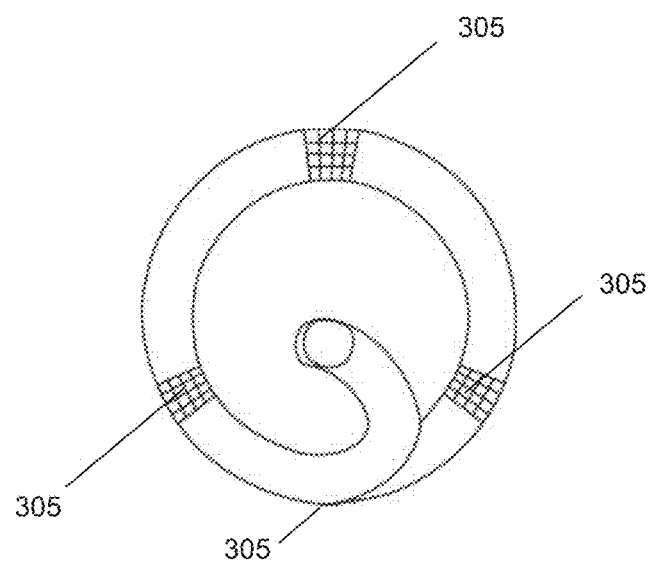
FIG. 3F shows an end-on view of the distal portion of a single helix ablation catheter according to the embodiment shown in FIG. 3D from the delivery direction of the lead, displaying only the first turn of the coil with electrodes 305.
Figure 3G:
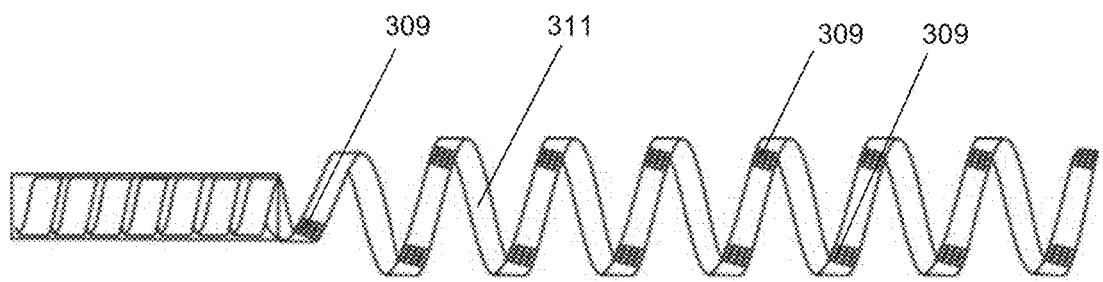
FIG. 3G shows an elevational view of the distal portion of a single helix ablation catheter according to an embodiment of the present invention wherein electrodes 309 are placed at 90° intervals along the helix length, and wherein the helical coil 311 itself is flattened.
Figure 3H:
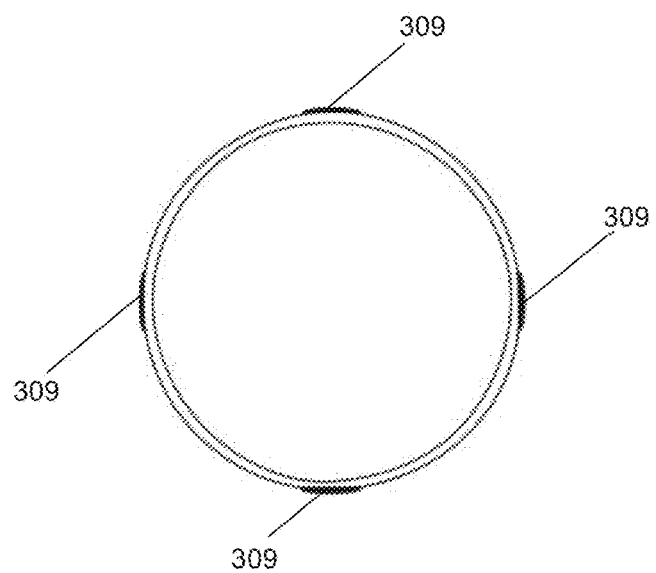
FIG. 3H shows the distribution of electrodes 309 in a single complete coil in the helix of the ablation catheter shown in FIG. 3G.
Figure 3I:
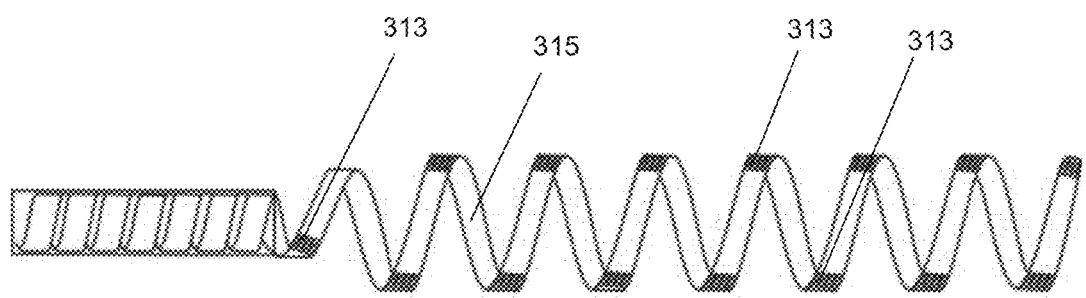
FIG. 3I shows an elevational view of the distal portion of a single helix ablation catheter according to the embodiment of the present invention wherein electrodes 313 are placed at 120° intervals along the helix length, and wherein the helical coil 315 itself is flattened.
Figure 3J:
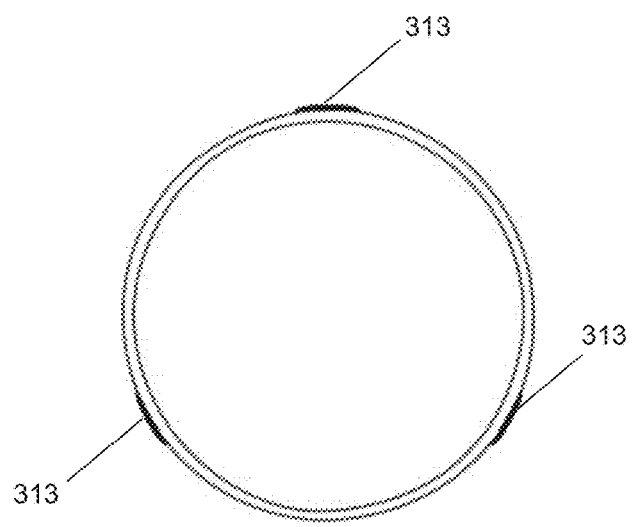
FIG. 3J shows the distribution of electrodes 313 in a single complete coil in the helix of the ablation catheter shown in FIG. 3I.
Figure 4A:
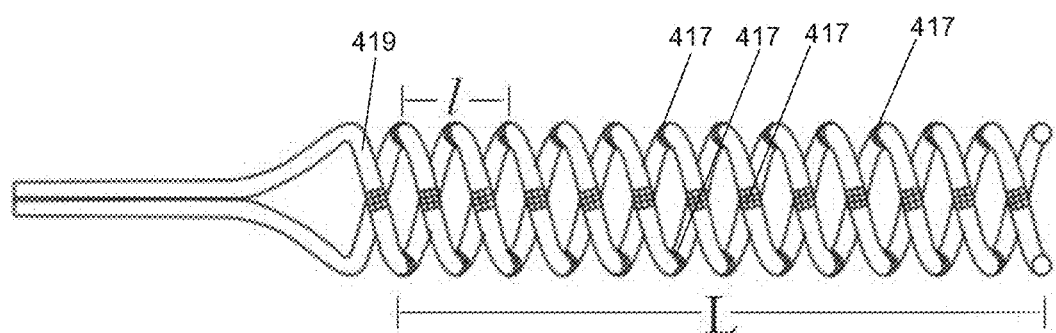
FIG. 4A shows an elevational view of a distal portion of a double helix ablation catheter according to an embodiment of the present invention wherein electrodes 417 are placed at 90° intervals along the length of each separate helix, wherein the helical coils 419 are round, and wherein "L" designates the length of the distal portion, and "l" designates the length of one turn of each helical coil.
Figure 4B:
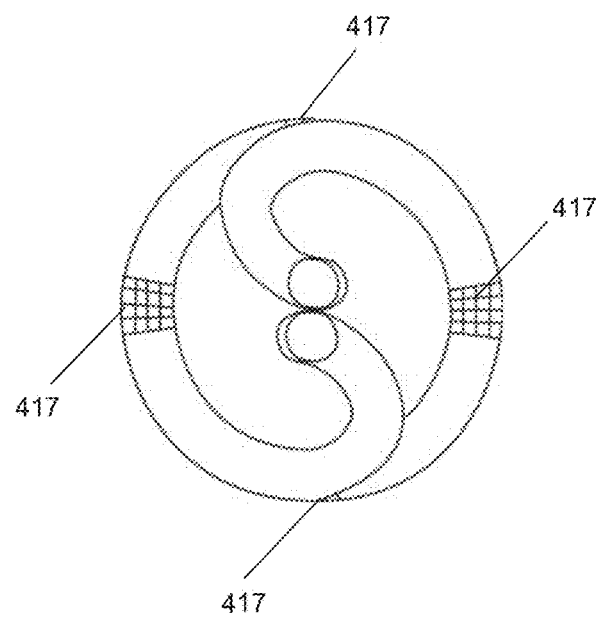
FIG. 4B shows an end-on view of the distal portion of a double-helix ablation catheter according to the embodiment shown in FIG. 4A from the delivery direction of the lead, displaying only the first turn of each coil with electrodes 417.
Figure 4C:
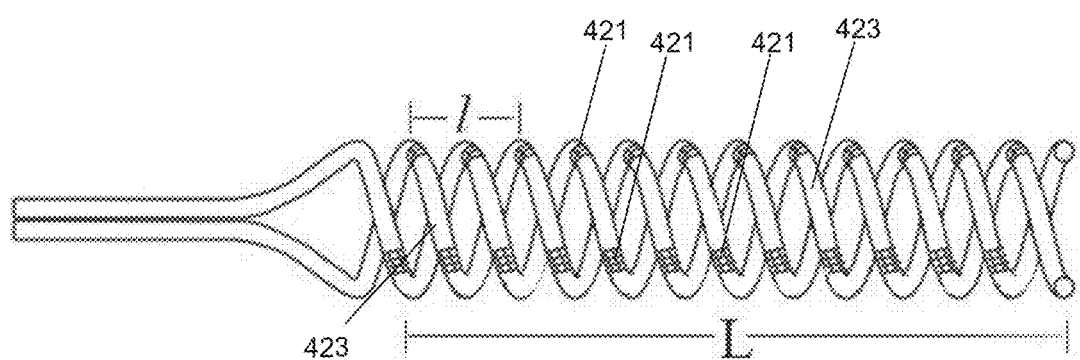
FIG. 4C shows an elevational view of a distal portion of a double helix ablation catheter according to an embodiment of the present invention wherein electrodes 421 are spaced at 120° intervals along the length of each separate helix, wherein the helical coils 423 are round, and wherein "L" designates the length of the distal portion, and "l" designates the length of one turn of each helical coil.
Figure 4D:
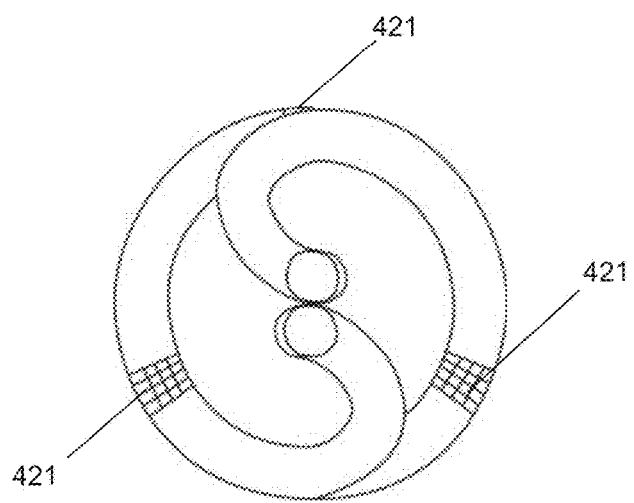
FIG. 4D shows an end-on view of the distal portion of a double-helix ablation catheter according to the embodiment shown in FIG. 4C from the delivery direction of the lead, displaying only the first turn of each coil with electrodes 421.
Figure 4E:
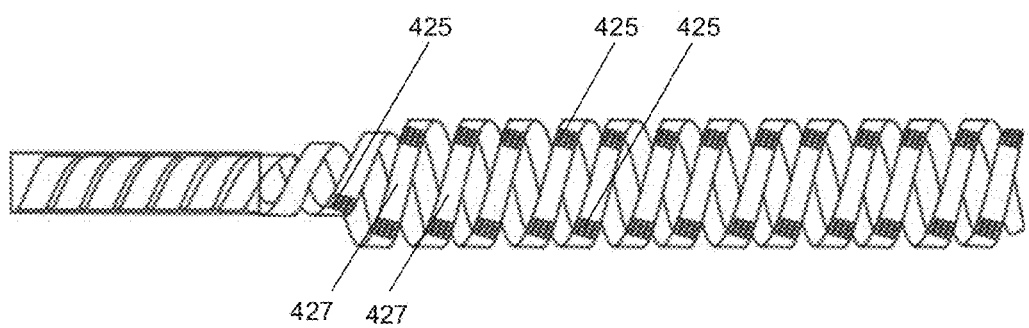
FIG. 4E shows an elevational view of the distal portion of a double helix ablation catheter according to an embodiment of the present invention wherein electrodes 425 are spaced at 90° intervals along the length of each separate helix, and wherein the helical coils 427 are flat.
Figure 4F:
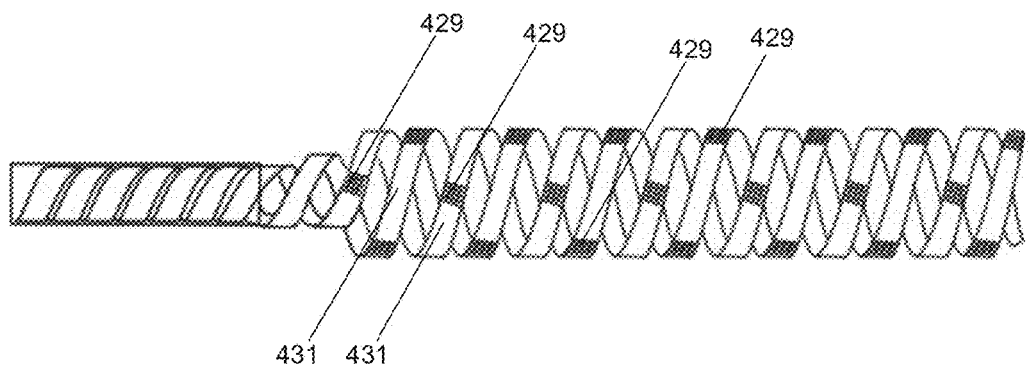
FIG. 4F shows an elevational view of the distal portion of a double helix ablation catheter according to an embodiment of the present invention wherein electrodes 429 are spaced at 120° intervals along the length of each separate helix, and wherein the helical coils 431 are flat.

FIG. 2 is a flow chart illustrating the steps of the method for determining the presence of any functional sympathetic or parasympathetic nerve innervating a selected area of an arterial wall.

At step 1, physiological signals from sensor 103 are continuously recorded by device 104 to produce a reliable baseline reflective of any instantaneous changes in the signals.

Energy is then delivered by one of the electrodes in device 101 to the area on the arterial wall that this electrode is in contact with (Step 2). Sensor 103 detects any physiological change caused by the energy delivered, and the change is recorded as signals which are then sent to device 104. (Step 3)

In step 4, device 104 determines the deviation of the physiological signals from the baseline of step 1 and, in step 5, determines the type of nerves innervating the area on the arterial wall based on the deviation from the baseline information.

In one embodiment, the physiological signals detected by sensor 103 comprises one or more of blood pressure, heart rate, biochemical levels, cardiac electrical activity, muscle activity, skeletal nerve activity, action potential of cells and other observable body reactions as a result of the above such as pupil response and vascular constriction.

In an embodiment, the dosage of energy delivered in step 2 is adjustable to induce different interactions with a targeted nerve such as nerve stimulation or nerve ablation.

In certain embodiments, the values of the physiological signals are measured using other external devices and inputted into device 104 prior to the energy delivery to replace the baseline formed by device 104.

In one embodiment, the changes in physiological parameters are detected during or after the energy delivery process in step 2. In another embodiment, the changes in physiological parameters are in the form of numerical values or waveforms. In further embodiments, the deviation from baseline of step 1 is evaluated by subtracting the baseline of step 1 from the signals.

In one embodiment, the empirically pre-determined set of values could be obtained from sets of clinical data or deduced from the experience of clinical physicians. In some embodiments, an area on the arterial wall is considered to be innervated with sympathetic nerves when energy delivered to the area causes an increase in heart rate by 10 beats per minute and/or an increase in blood pressure by 6 mmHg. In other embodiments, an area on the arterial wall is considered to be innervated with parasympathetic nerves when energy delivered to the area causes a decrease in heart rate by 5 beats per minute and/or a decrease in blood pressure by 2 mmHg.

In a further embodiment, the results of step 5 will be displayed on indicator 105.

In one embodiment, the method is used for identifying the suitable sites for nerve ablation in the arterial wall to disrupt baroreflex via sympathetic and parasympathetic nervous systems. In another embodiment, the method provides indication of whether the ablation energy is delivered accurately to the targeted nerves in the arterial wall. In a further embodiment, the method is used for immediate post-procedural assessment of nerve ablation.

Figure 5A:
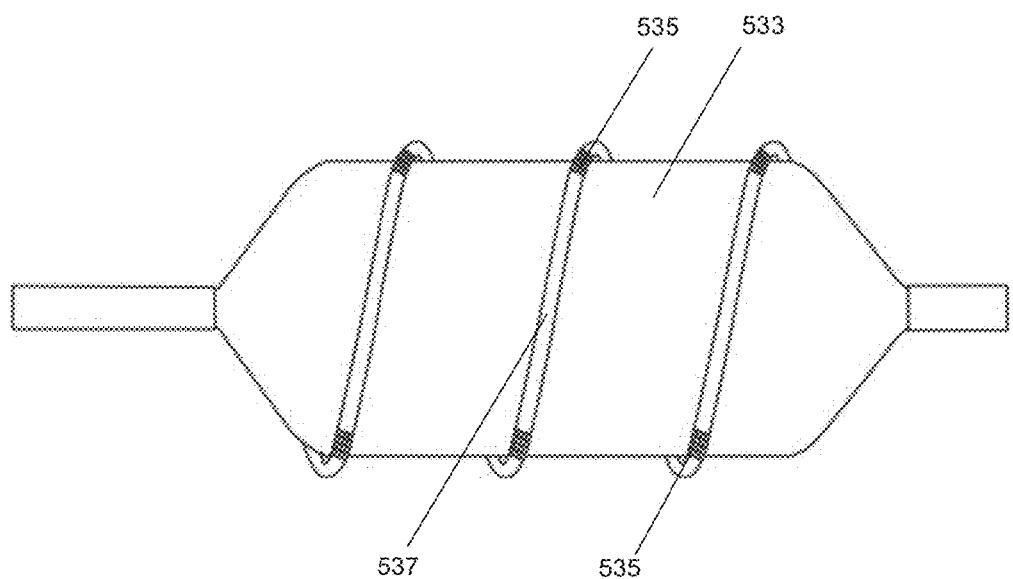
FIG. 5A shows an elevational view of a distal portion of a balloon ablation catheter according to an embodiment of the present invention, wherein the balloon 533 is inflated, and wherein electrodes 535 are evenly spaced at intervals along a helical coil 537 which is round in shape and wrapped around the balloon.
Figure 5B:
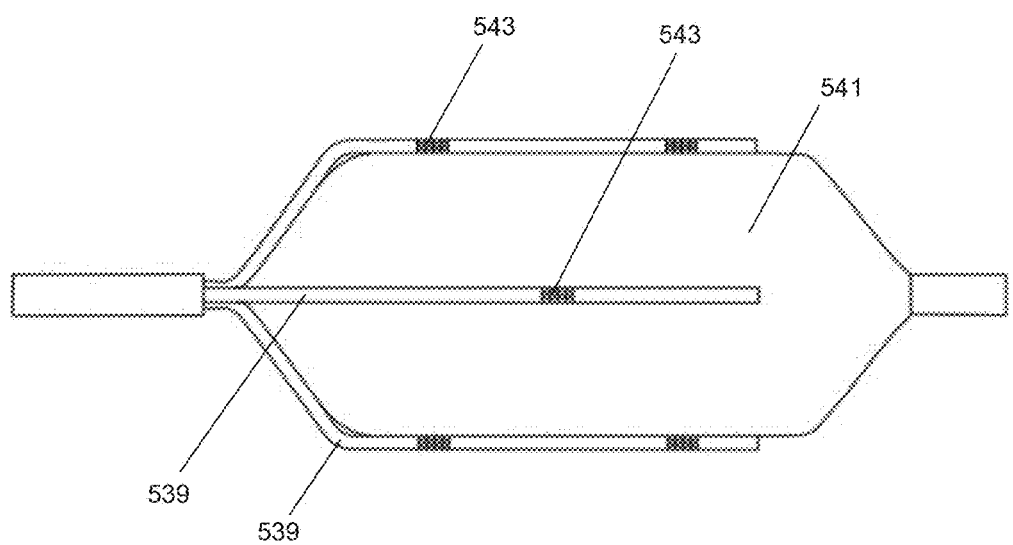
FIG. 5B shows an elevational view of a distal portion of a balloon ablation catheter according to an embodiment of the present invention incorporating an umbrella-like component 539 encapsulating the balloon 541, wherein the balloon is inflated, and wherein electrodes 543 are spaced at intervals along the umbrella encapsulating the balloon.

The present invention also provides for specially-designed catheters with a steerable distal end (i.e. the catheter tip) in shapes customized to renal architecture, possessing one or more electrodes to map renal nerve distribution, to perform renal ablations and to perform angiography. In certain embodiments, the electrodes of such catheters are sequentially spaced along the length of the catheter tip, where the electrode faces make contact with segmented portions of the renal artery lumen. In certain embodiments, the shape of the catheter tip is a single helix wherein the coil of the helix is either round or flat in shape (FIGS. 3A-J). In other embodiments, the catheter tip is a double helix wherein the coils of the helices are either round or flat in shape (FIGS. 4A-F). In further embodiments, the catheter tip may comprise a balloon around which is wrapped a helical coil, wherein spaced along the length of the helical coil are electrodes (FIG. 5A); alternately, the catheter tip may comprise a balloon around which is an umbrella component encapsulating the balloon, and wherein spaced along the umbrella component are electrodes (FIG. 5B). In variations of both embodiments shown in FIGS. 5A and 5B, the coil or umbrella component may be either round or flat in shape; consequently the electrodes spaced along the length of the coil or umbrella may be round or flat in shape, depending upon the underlying shape of the coil or umbrella.

Figure 6A:
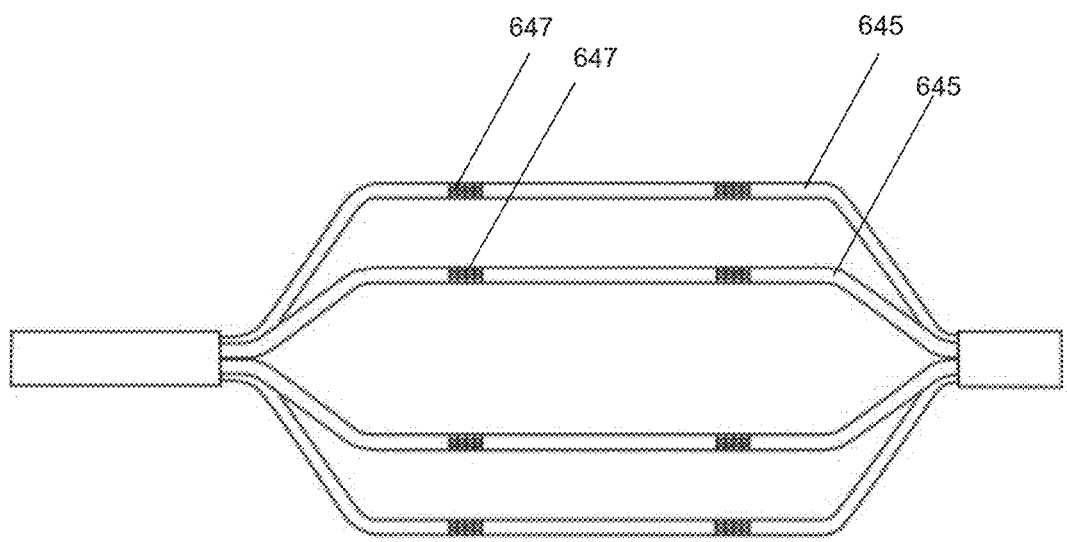
FIG. 6A shows an elevational view of a distal portion of an ablation catheter according to an embodiment of the present invention incorporating a closed-end umbrella like frame 645 wherein electrodes 647 are spaced at intervals along the umbrella like frame.
Figure 6B:
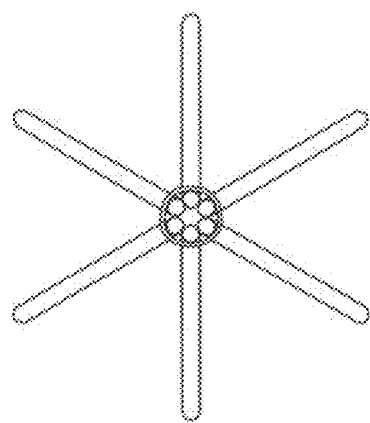
FIG. 6B shows an end-on view of the distal portion of an ablation catheter according to the embodiment like shown in FIG. 6A from the delivery direction of the lead.
Figure 6C:
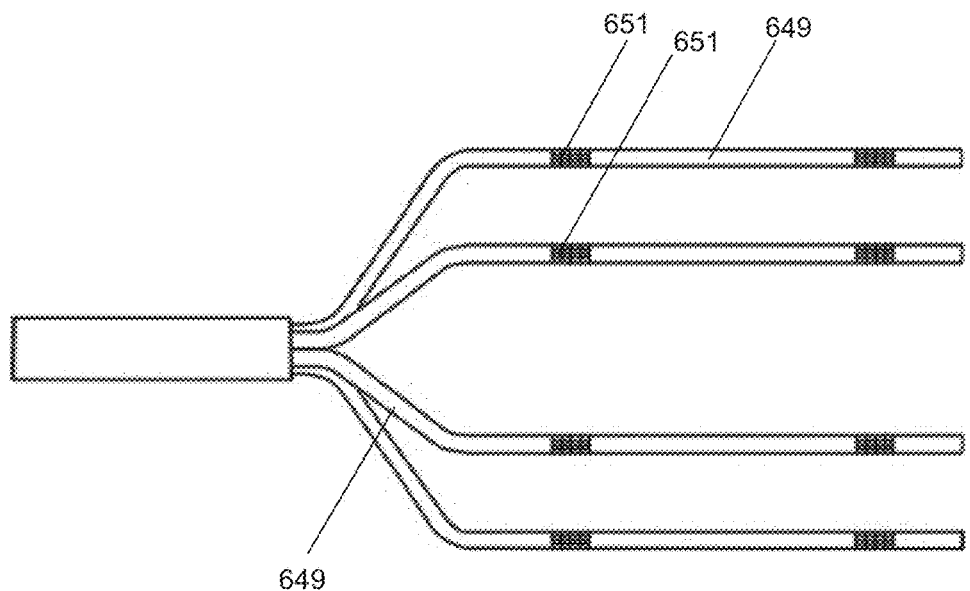
FIG. 6C shows an elevational view of a distal portion of an ablation catheter according to an embodiment of the present invention incorporating an open-end umbrella like frame 649 wherein electrodes 651 are spaced at intervals along the umbrella frame.
Figure 6D:
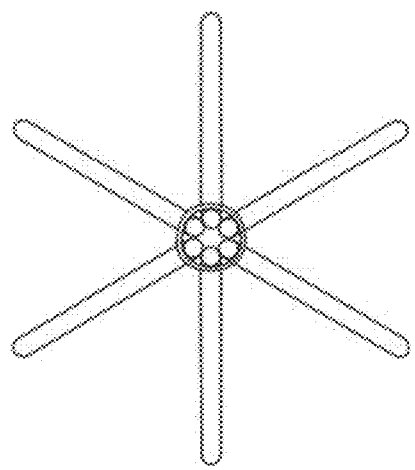
FIG. 6D shows an end-on view of the distal portion of an ablation catheter from the delivery direction of the lead.

In further embodiments, the catheter tip may comprise an umbrella shape or frame with a closed end (FIGS. 6A-B), or umbrella with an open end (FIG. 6C-D).

Figure 7A:
FIG. 7A shows an elevational view of a distal portion of an ablation catheter according to an embodiment of the present invention wherein a single electrode 755 is located at a steerable catheter tip 753.
Figure 7B:
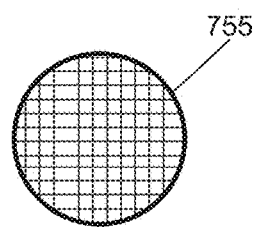
FIG. 7B shows an end-on view of the distal portion of an ablation catheter according to the embodiment shown in FIG. 7A from the delivery direction of the lead, displaying the electrode 755.

In another embodiment, the catheter has a steerable catheter tip with a single electrode at its tip (FIG. 7A-B).

In certain embodiments, the above catheter tips may be introduced into the arterial architecture to perform the functions of a stent.

In one embodiment, the diameter of these catheter tips, d, may vary from 0.5 mm to 10 mm; the length of the catheter tips, L, may vary from 20 mm to 80 mm; the diameters of coil, D, may vary from 3.0 mm to 7.5 mm; the distances between each coil, l, may vary from 4 mm to 6 mm; the numbers of coils may vary from 3.3 to 20; and the fully uncoiled lengths of the coils may vary from 31 mm to 471 mm.

The electrodes of the catheters may be activated independently of one another or can be activated in any combination to emit electrical stimulation or radiofrequency energy. The electrodes each have dual functions of delivering electrical stimulation or radiofrequency energy. Electrical stimulation is used to identify and map segments of renal artery lumen beneath which lie renal nerves of importance. Said identification and mapping is accomplished through the monitoring of a physiological response or responses to the applied electrical stimulation, such as changes in blood pressure response and heart rate or muscle sympathetic nerve activity (Schlaich et al., NEJM 2009), or renal norepinephrine spillover (Esler et al. 2009, and Schlaich et al., J Htn. 2009), wherein changes in physiological response indicate the presence of an underlying sympathetic nerve distribution in the vicinity of the activated electrode. In another embodiment, individual electrodes of the catheters may be activated in physician operator-selected combinations in order to assess maximal physiological response, and the consequent locations of underlying renal nerves. The electrodes of the catheters are able to emit not just electrical current of sufficient strength to stimulate renal nerve, but thermal energy such as radiofrequency energy to ablate underlying renal nerve tissue based on renal nerve mapping results. In other embodiments, separate electrodes of the catheters can be selectively activated to emit ablative energy such as high radiofrequency energy wherein the choice of the activated electrodes is based upon the results of the mapping of the nerves. In further embodiments, based on the mapping of the renal nerves, ablative techniques using other types of ablative energy such as laser energy, high intensive focused ultrasound or cryoablative techniques can be utilized on renal artery walls to ablate the sympathetic renal nerves.

In certain embodiments, these catheters are interchangeably used with existing radiofrequency generators which are presently utilized with existing cardiac catheter systems.

In one embodiment, the aforementioned catheter systems may be utilized with any variety of acceptable catheter guidewire previously inserted into the patient's body to guide the catheter tip to the desired location. They may also be used with devices and other instruments that may be used to facilitate the passage of like devices within the cardiovascular and renal vascular systems, such as sheaths and dilators. When required, the aforementioned catheter systems may also be utilized with a puller wire to position the catheter tip.

The present invention also provides methods of using the catheters described herein to map renal nerve distribution, comprising the steps of using electrical stimulation while monitoring changes in physiological responses, such as blood pressure and heart rate, to map renal nerve distribution and identify ablation spots within renal arteries for ideal denervation of renal nerves. These methods comprise activating the independent electrodes of the described catheters to emit an electrical charge to stimulate the underlying renal nerve while monitoring physiological responses such as blood pressure and heart rate; the presence of changes in physiological response indicate the presence of an underlying sympathetic nerve in the vicinity of the activated electrode and a superior location for ablation. An agglomeration of mapping data may take the form of a clinically useful guide respecting renal nerve distribution to assist clinicians in performing ablation.

In one embodiment, the tip of said catheter is optionally moved in a blood vessel according to a specified protocol in order to make contact with desired portions of the renal artery lumen. In one embodiment, the optional protocol for moving the catheter tip in the above method comprises moving the stimulatory or ablative section of the catheter tip from the half of the renal artery closer to the interior of the kidney to the half of the renal artery closer to the aorta and applying one or more electrical stimulation to each of the two halves.

In another embodiment, the optional protocol for moving the catheter tip comprises turning the stimulatory or ablative section of the catheter tip within the renal artery in the following sequence: (a) turning from the anterior wall to the posterior wall of the artery; (b) turning from the posterior wall to the superior wall of the artery; and (c) turning from the superior wall to the inferior wall of the artery, wherein each turn is 90° or less. In one embodiment, one or more electrical stimulations are applied after each turning of the catheter tip within the renal artery.

In one embodiment, the electrical stimulation applied falls within the following parameters: (a) voltage of between 2 to 30 volts; (b) resistance of between 100 to 1000 ohms; (c) current of between 5 to 40 milliamperes; (d) applied between 0.1 to 20 milliseconds.

The present invention also provides a method of ablating renal nerves to treat disease caused by systemic renal nerve hyperactivity, comprising the steps of: (a) applying the mapping method described herein to map renal nerves; (b) applying radiofrequency energy through the catheter to site-specific portions of the renal artery lumen to ablate the mapped renal nerves; and (c) applying stimulation again to assess the effectiveness of ablation. In further embodiments, based on the mapping of the renal nerves, other ablative techniques generally known in the art can be utilized on renal artery walls to ablate the sympathetic renal nerves, e.g. ablative techniques using other ablative energy such as laser energy, high intensive focused ultrasound or cryoablative techniques.

The present invention provides for a catheter adapted to be used in a method for locating or identifying a functional nerve innervating the wall of a blood vessel in a subject, comprising a shaft, wherein the proximal end of said shaft is configured to be connected to an energy source, and the distal end (catheter tip) of said shaft is in the form of a single helix, double helix or multiple prongs having one or more electrodes.

In one embodiment, said catheter comprises one or more electrodes that are configured to emit energy sufficient to stimulate or ablate a nerve on said vessel. In a further embodiment, said electrodes may be activated independently of one another.

In one embodiment, said catheter is between 1 and 2 m in length, wherein the catheter tip is between 2 and 8 cm in length, and between 0.5 mm and 10 mm in diameter.

In one embodiment, said catheter contains helical coils or prongs which are substantially round or flat in shape, and the electrodes are spaced along the length of said coils or prongs, wherein said electrodes are embedded in said coils or prongs, or lie on the surface of said coils or prongs. In one embodiment, the prongs are rejoined at the distal end. In yet another embodiment, the electrodes are evenly spaced along the length of said coils at 90° or 120° from each other.

In one embodiment, said catheter has a catheter tip that is configured to hold a balloon inflatable to fill the space within the coil of said helix or prongs.

The present invention also provides a method of using a catheter to locate or identify a functional nerve innervating the wall of a blood vessel in a subject, comprising the steps of: a) inserting said catheter into said blood vessel and activating the electrodes on the catheter to deliver energy to one or more locations on said vessel wall sufficient to change one or more physiological parameters associated with the innervation of said vessel by a sympathetic or parasympathetic nerve; and b) measuring said one or more physiological parameters after each energy delivery, and determining the change from the corresponding parameters obtained without energy delivery to said vessel; wherein a lack of change in said physiological parameters in step b indicates the absence of a functional nerve at the location of energy delivery, a significant change in said physiological parameters in step b indicates the presence of a functional nerve at the location of energy delivery, and the direction of change in said physiological parameters in step b determines the nerve to be sympathetic or parasympathetic at the location of energy delivery. It is to be understood that a lack of change means that the change would be considered by someone skilled in the art to be negligible or statistically insignificant, and a significant change means that the change would be considered by someone skilled in the art to be meaningful or statistically significant.

In one embodiment, said vessel is an artery, including a renal artery. In one embodiment, the functional nerve is related to baroreflex. In one embodiment, the location where energy is delivered is an area where a nerve has been ablated, wherein a lack of change in said physiological parameters in step b confirms nerve ablation. In another embodiment, the subject used is a human or non-human animal. In another embodiment, the physiological parameters described are selected from blood pressure, heart rate, cardiac electrical activity, muscle activity, skeletal nerve activity, action potential of cells, pupil response, electromyogram, vascular constriction, and levels of biochemicals selected from epinephrine, norepinephrine, renin-angiotensin II and vasopressin. In yet another embodiment, said energy is adjustable and consists of one or more of electrical, mechanical, ultrasonic, radiation, optical and thermal energies. In one embodiment, said energy causes nerve stimulation or nerve ablation. In another embodiment, the functional nerve is a sympathetic or parasympathetic nerve. In yet another embodiment, the energy delivered falls within the following ranges: a) voltage of between 2 and 30 volts; b) resistance of between 100 and 1000 ohms; c) current of between 5 and 40 milliamperes; and d) time of application between 0.1 and 20 milliseconds.

In one embodiment, the catheter used for insertion into a blood vessel is moved in the blood vessel in the following sequence: a) turning 90° or less from the anterior wall to the posterior wall of the artery; b) turning 90° or less from the posterior wall to the superior wall of the artery; and c) turning 90° or less from the superior wall to the inferior wall of the artery.

It will be appreciated by persons skilled in the art that the system and method disclosed herein may be used in nerve ablation of the renal artery to disrupt baroreflex via sympathetic and parasympathetic nervous systems but its application could be extended to any innervated vessels in the body.

The invention will be better understood by reference to the Experimental Details which follow, but those skilled in the art will readily appreciate that the specific examples are for illustrative purposes only and should not limit the scope of the invention which is defined by the claims which follow thereafter.

It is to be noted that the transitional term "comprising", which is synonymous with "including", "containing" or "characterized by", is inclusive or open-ended and does not exclude additional, un-recited elements or method steps.

EXAMPLE 1

Locating Nerves Innervating an Arterial Wall

A method to locate nerves innervating an arterial wall via examination of the changes in physiological parameters after the delivery of a suitable dose of energy was designed and executed in acute pig experiments. The aims of this experiments are:
1. To test currently existing cardiac ablation catheters (7F, B-Type, spacing 2-5-2 mm, CELSIUS® RMT Diagnostic/Ablation Steerable Catheter, Biosense Webster, Diamond Bar, Calif. 91765, USA) and a radiofrequency generator (STOCKERT 70 RF Generator, Model Stockert GmbH EP-SHUTTLE ST-3205, STOCKERT GmbH, Freiburg, Germany) for the purposes of renal nerve mapping and ablation.
2. To test renal nerve mapping via examination of changes in blood pressure and heart rate during emission of electrical stimulation at different sites within the lumen of the left and right renal arteries.
3. To determine the safe range of high radiofrequency energy to be emitted to renal arteries for renal nerve ablation via examination of visual changes of renal arterial walls and histology.
4. To use changes in blood pressure and heart rate as indices of efficient ablation of renal nerves during renal ablation.

Figure 8:
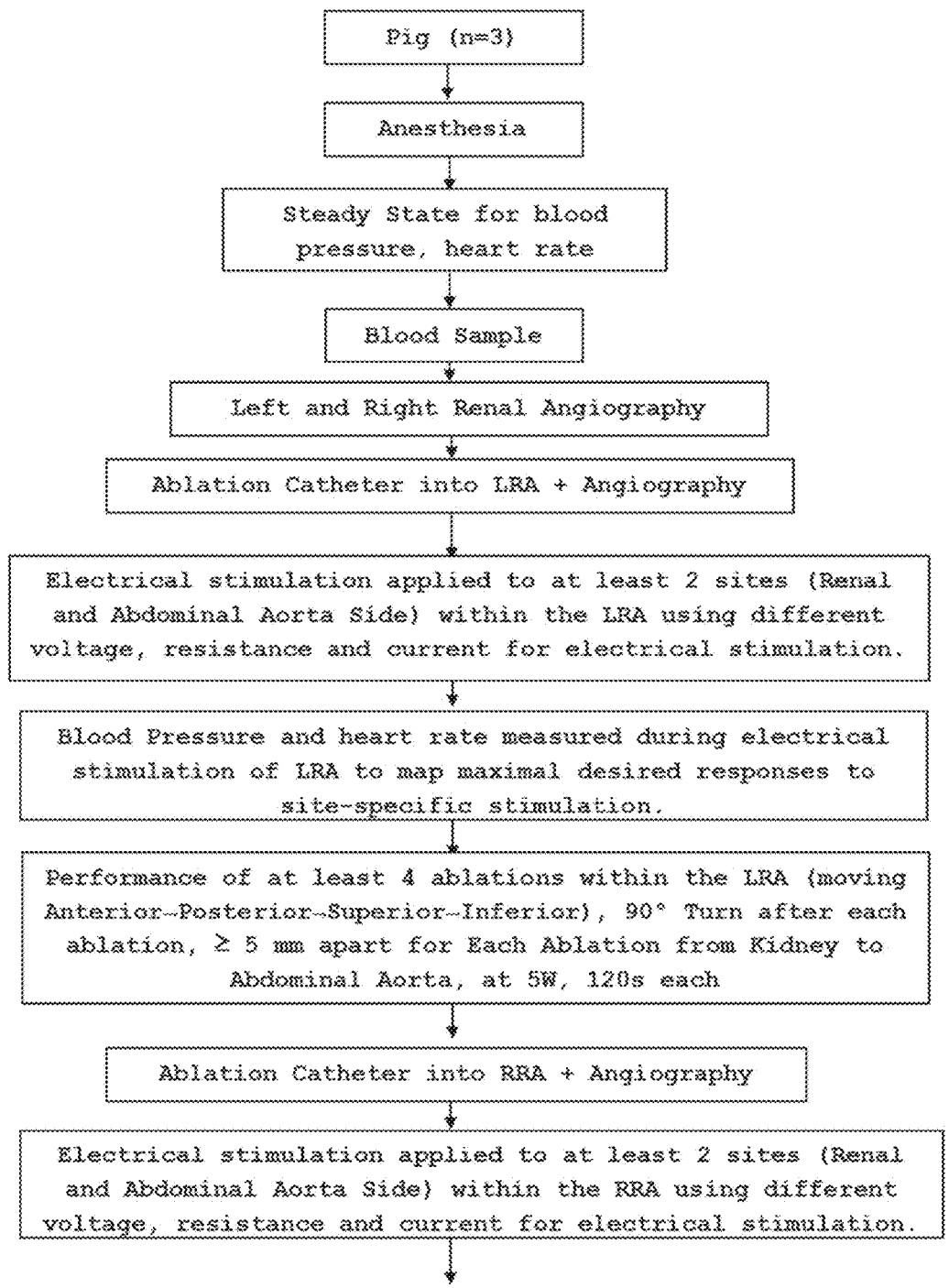
FIG. 8 shows the experimental setup for acute pig experiments used in nerve mapping experiments.
Figure 8:
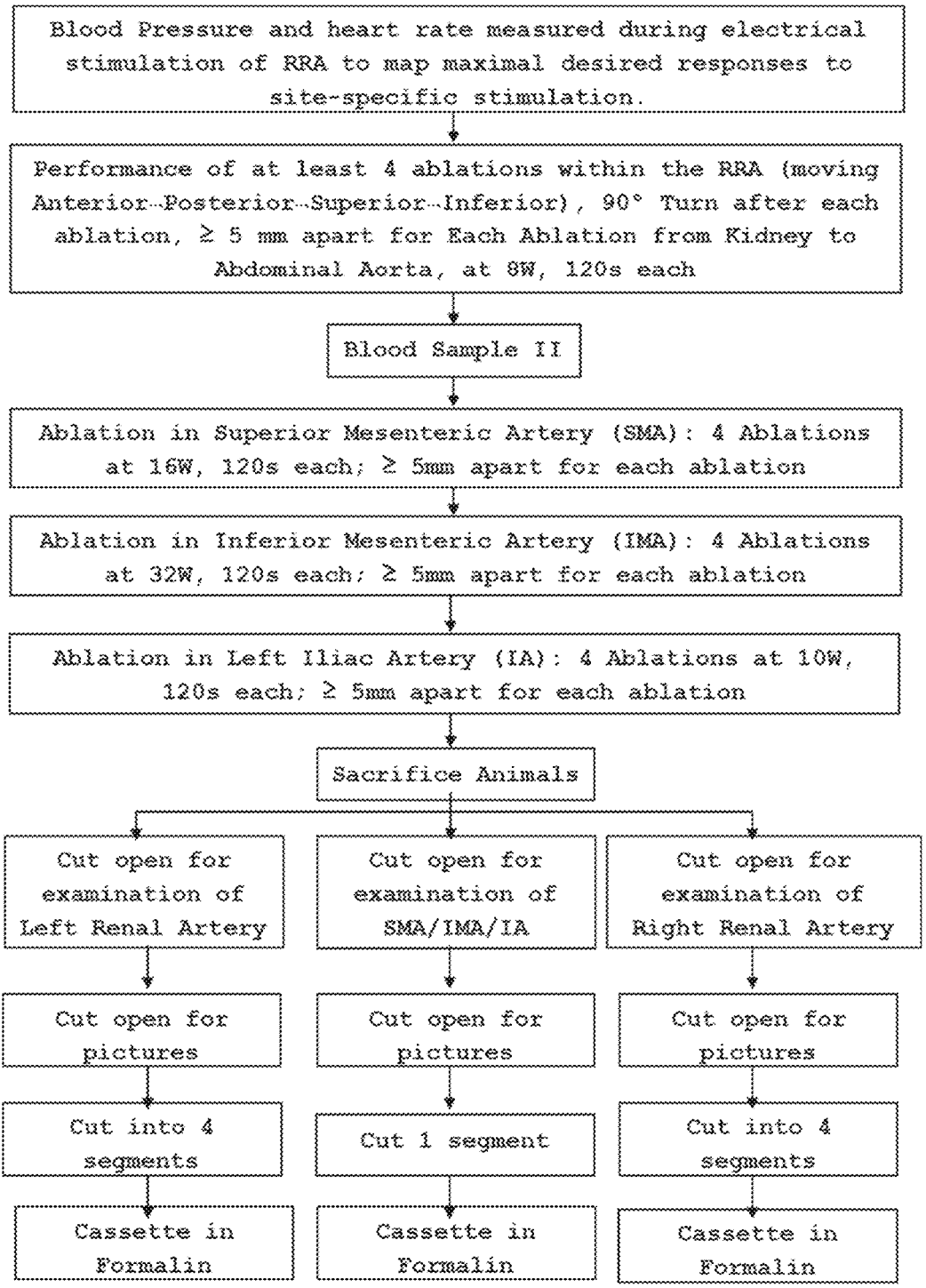
Figure 9A:
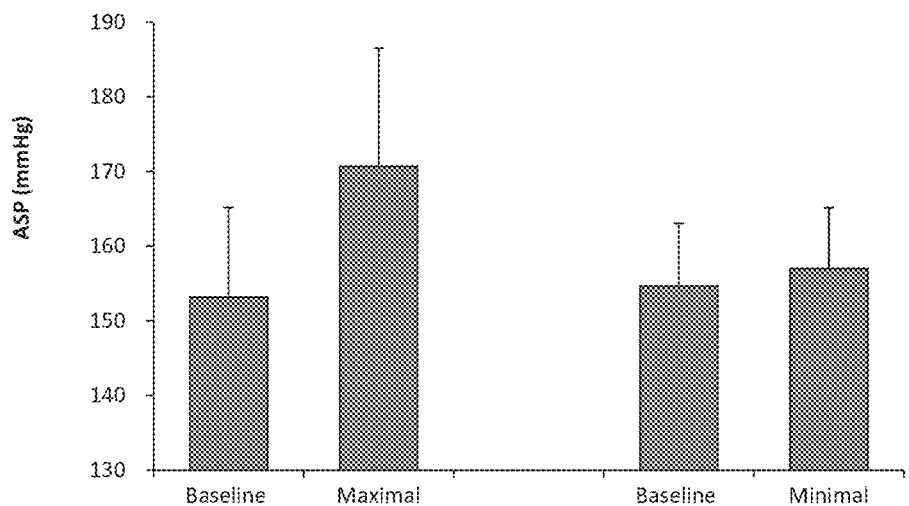
FIG. 9A shows Maximal and Minimal Effects of Left Renal Artery Stimulation on Arterial Systolic Pressure (ASP). Shown is arterial systolic pressure (ASP, as measured in mmHg) after an electrical stimulation in the left renal artery (LRA); baseline measures, as well maximal and minimal responses after the stimulation are shown.
Figure 9B:
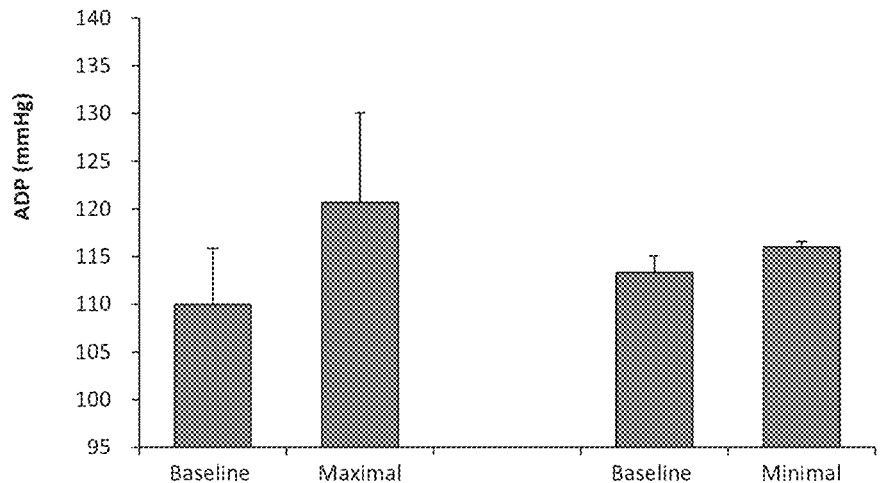
FIG. 9B shows Maximal and Minimal Effects of Left Renal Artery Stimulation on Arterial Diastolic Pressure (ADP). Shown is arterial diastolic pressure (ADP, as measured in mmHg) after an electrical stimulation in the left renal artery (LRA); baseline measures, as well as maximal and minimal responses after the stimulation are shown.
Figure 9C:
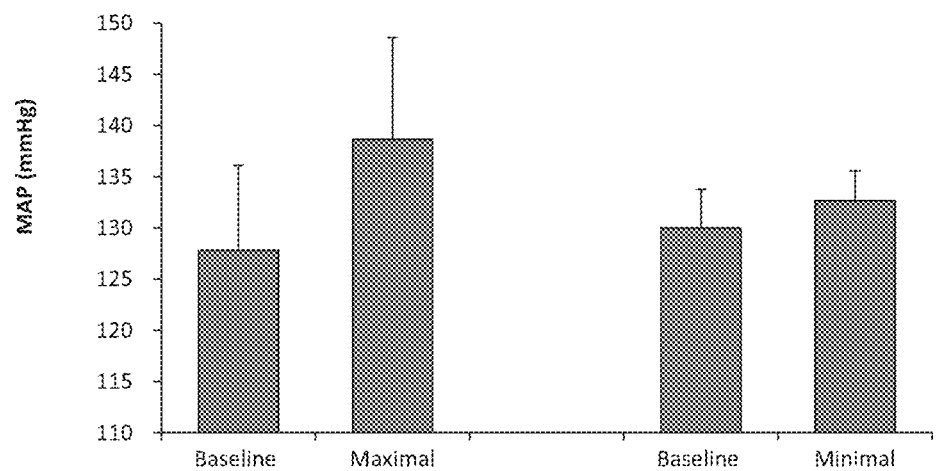
FIG. 9C shows Maximal and Minimal Effects of Left Renal Artery Stimulation on Mean Arterial Pressure (MAP). Shown is mean arterial pressure (MAP, as measured in mmHG) after an electrical stimulation in the left renal artery (LRA); baseline measures, as well as maximal and minimal responses after the stimulation are shown.
Figure 9D:
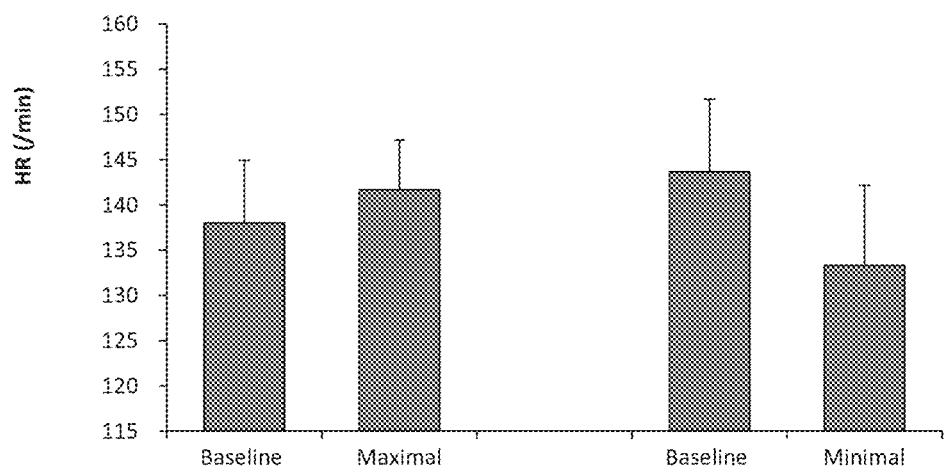
FIG. 9D shows Maximal and Minimal Effects of Left Renal Artery Stimulation on Heart Rate(HR). Shown are maximal and minimal changes in heart rate after left renal artery (LRA) electrical stimulation; baseline measures, as well as maximal and minimal heart rates after the stimulation are shown.
Figure 10A:
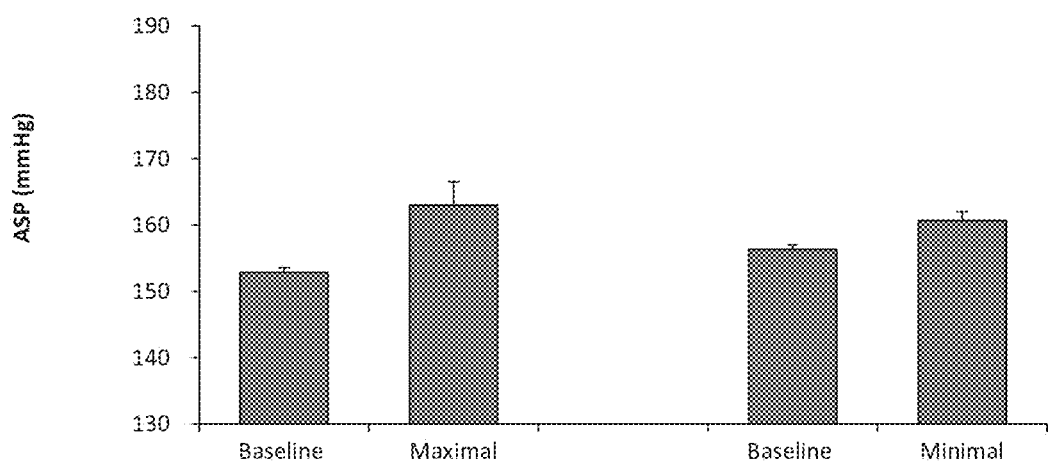
FIG. 10A shows Maximal and Minimal Effects of Right Renal Artery Stimulation on Arterial Systolic Pressure (ASP). Shown is arterial systolic pressure (ASP, as measured in mmHg) after stimulation in the right renal artery (RRA); baseline measures, as well maximal and minimal responses after an electrical stimulation are shown.
Figure 10B:
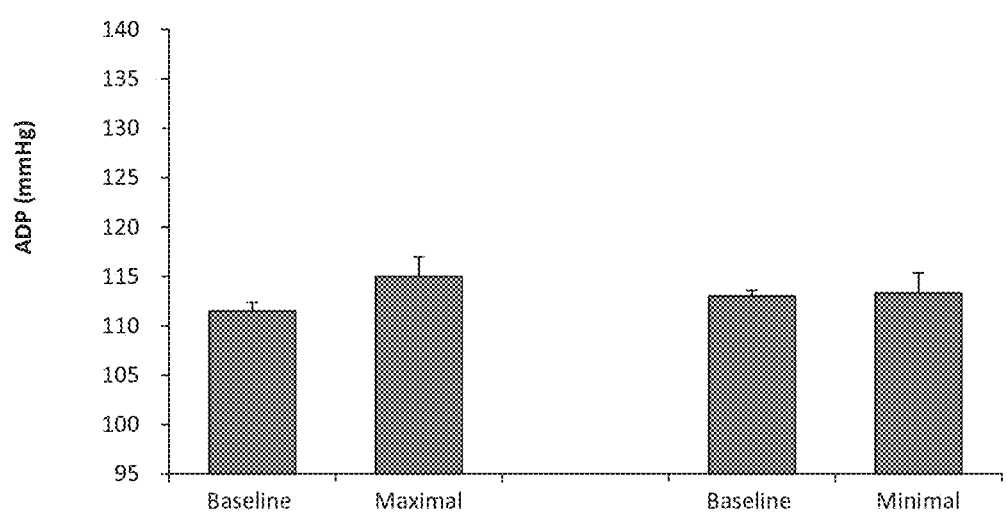
FIG. 10B shows Maximal and Minimal Effects of Right Renal Artery Stimulation on Arterial Diastolic Pressure (ADP). Shown is arterial diastolic pressure (ADP, as measured in mmHg) after an electrical stimulation in the right renal artery (RRA); baseline measures, as well as maximal and minimal responses after the stimulation are shown.
Figure 10C:
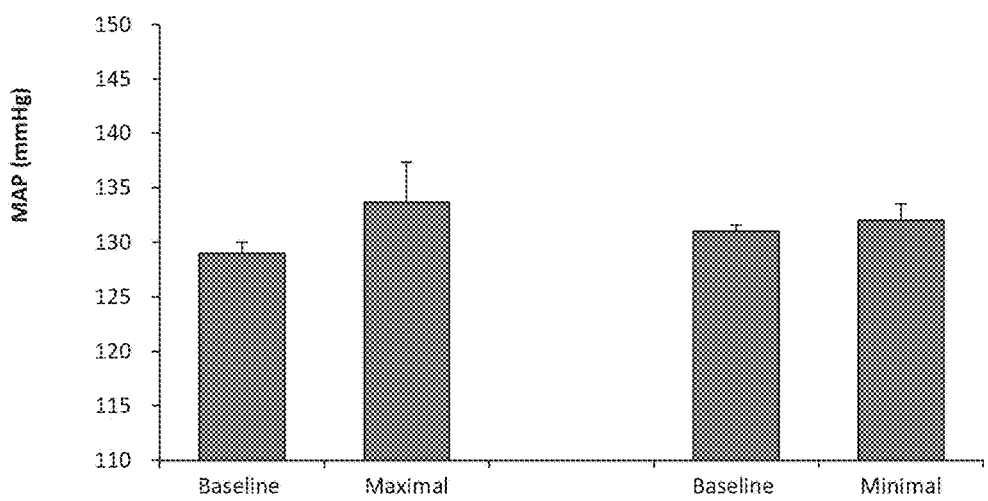
FIG. 10C shows mean arterial pressure (MAP, as measured in mmHg) after an electrical stimulation in the right renal artery (LRA); baseline measures, as well as maximal and minimal responses after the stimulation are shown.
Figure 10D:
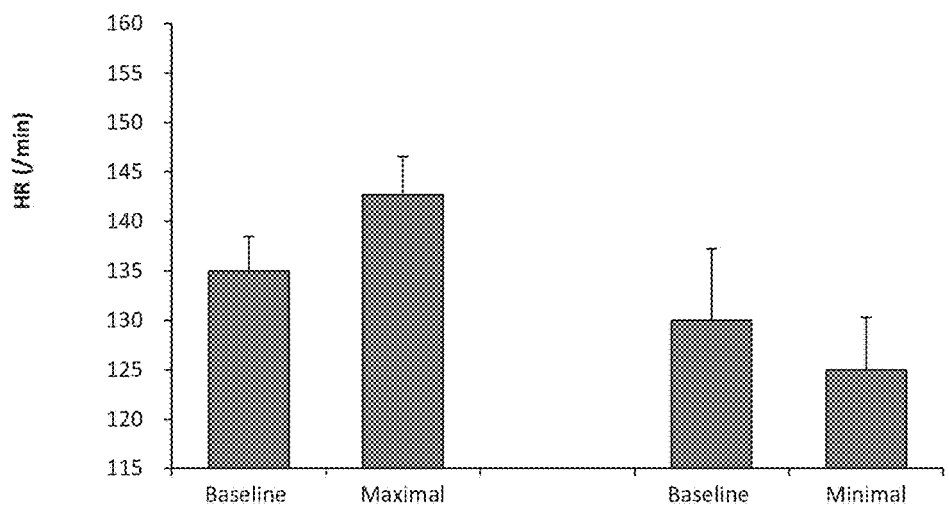
FIG. 10D shows Maximal and Minimal Effects of Right Renal Artery Stimulation on Heart Rate (HR). Shown are maximal and minimal changes in heart rate after right renal artery (RRA) electrical stimulation; baseline measures, as well as maximal and minimal heart rates after the stimulation are shown.

Three pigs (body weight from 50-52 kg) were anesthetized with intravenous injection of sodium pentobarbital at 15 mg/kg. The physiological parameters: systolic blood pressure, diastolic blood pressure, mean arterial pressure and heart rate were monitored. The experimental design and protocol are illustrated in FIG. 8.

The ablation catheter used in this set of experiments was the 7F,B-Type, spacing 2-5-2 mm, CELSIUS® RMT Diagnostic/Ablation Steerable Catheter (Biosense Webster, Diamond Bar, Calif. 91765, USA) and a Celsius radiofrequency generator (STOCKERT 70 RF Generator, Model Stockert GmbH EP-SHUTTLE ST-3205, STOCKERT GmbH, Freiburg, Germany).

Baselines for systolic, diastolic and mean arterial blood pressure and heart rate were measured before the delivery of electrical energy to different areas of the renal arterial wall. Mean arterial blood pressure and heart rate were then measured 5 seconds to 2 minutes after the delivery of energy to note for any effects. By recognizing that a significant change in blood pressure and heart rate to be associated with nerve stimulation, it was found that, although the segment of the arterial wall that is innervated varies in each animal, the method described herein has correctly located these areas in each of the animals giving a map of the innervated regions in the renal artery.

EXAMPLE 2

Relationship Between Physiological Parameters and the Nerves Innervating an Arterial Wall In order to demonstrate that energy delivered to different locations on an arterial wall may result in different effects on physiological parameters such as blood pressure and heart rate, and such characteristics can be capitalized on to identify the type of nerve innervating an arterial wall, electrical energy was delivered to the innervated areas on the renal arterial walls of the pig model according to several strategies. Detailed parameters on the electrical energy delivered to Pig #1, Pig #2 and Pig #3 are shown in Table 1, Table 2 and Table 3 respectively.

In Pig #1, four separate stimulations took place in the left renal artery and two separate stimulations were performed in the right renal artery. As preliminary approaches, on the abdominal side of the left renal artery, two separate doses of electrical energy were delivered: one to the anterior wall and one to the posterior wall of the artery. On the kidney side of the left renal artery, two separate doses of electrical energy were delivered: one to the anterior wall and one to the posterior wall of the artery. Different effects of these energies on blood pressure and heart rate were observed. In the right renal artery, one dose of electrical energy was delivered to the renal artery on the abdominal side and the kidney side, respectively. The same stimulation strategy was used for Pig #2 and Pig #3.

The electrical energy delivered to different locations in the renal artery caused different effects on the systolic blood pressure, diastolic blood pressure, mean blood pressure and heart rate in all of the pigs tested. For instance, in response to the electrical energy delivered to the left kidney, the maximal change in systolic blood pressure was respectively 19.5 mmHg and 29 mmHg in Pig #1 and Pig #3; the minimal change of systolic blood pressure was respectively 2 mmHg and 1 mmHg in Pig #1 and Pig #3. However, in Pig #2, changes in systolic blood pressure were consistent when the electrical energy was delivered to either the abdominal aorta side or the kidney side. Furthermore, the stimulation location which caused the maximal effect or minimal effect varied from animal to animal, indicating that the distribution of renal autonomic nerves is not consistent between animals. These phenomena in systolic blood pressure, diastolic blood pressure, mean arterial blood pressure and heart rate during delivery of electrical energy to wall of the left renal artery were observed and further summarized in Table 4A, 4B, 4C and 4D, respectively. Similar phenomenon in systolic blood pressure, diastolic blood pressure, mean arterial blood pressure and heart rate during electrical stimulation in the right renal artery were also observed and further summarized in Table 5A, 5B, 5C and 5D, respectively.

These data provide proof of concept for locating and identifying nerves innervating an arterial wall—specifically, that a substantial physiological response, in this case, the maximal increase or decrease in measured blood pressure, was induced by delivery of electrical energy via a catheter placed at a defined location where renal nerve branches are abundantly distributed. Averaged data (mean±SD) calculated from Table 4A-D and Table 5A-D are graphically represented in FIG. 9 and FIG. 10, inclusive of all sub-figures.

TABLE 1

Renal Nerve Stimulation for Mapping
Pig #1:

| Renal Artery | Stimulation Site | | Stimulation Parameters |
|---|---|---|---|
| Left | Kidney side | Anterior Wall | 15 V; 0.4 ms; 400 Ohm; 17 mA |
| | | Posterior Wall | 15 V; 0.4 ms; 400 Ohm; 28 mA |
| | Abdominal Aorta Side | Anterior Wall | 15 V; 0.2 ms; 400 Ohm; 28 mA |
| | | Posterior Wall | 15 V; 0.2 ms; 540 Ohm; 28 mA |
| Right | Kidney side | | 15 V; 0.2 ms; 600 Ohm; 25 mA |
| | Abdominal Aorta Side | | 15 V; 0.2 ms; 520 Ohm; 25 mA |

TABLE 2

Renal Nerve Stimulation for Mapping
Pig #2:

| Renal Artery | Stimulation Site | Stimulation Parameters |
|---|---|---|
| Left | Kidney side | 15 V; 0.2 ms: 580 Ohm: 26 mA |
| | Abdominal Aorta Side | 15 V; 0.2 ms: 480 Ohm; 28 mA |
| Right | Kidney side | 15 V; 0.2 ms: 520 Ohm; 28 mA |
| | Abdominal Aorta Side | 15 V; 0.2 ms; 500 Ohm; 28 mA |

TABLE 3

Renal Nerve Stimulation for Mapping
Pig #3:

| Renal Artery | Stimulation Site | Stimulation Parameters |
|---|---|---|
| Left | Kidney side | 15 V; 9.9 ms; 800 Ohm; 28 mA |
| | Abdominal Aorta Side | 15 V; 9.9 ms; 800 Ohm; 28 mA |
| Right | Kidney side | 15 V; 9.9 ms; 800 Ohm; 28 mA |
| | Abdominal Aorta Side | 15 V; 9.9 ms; 800 Ohm; 28 mA |

TABLE 4A

Changes in Systolic Blood Pressure (SBP) During Electrical Stimulation in Left Renal Artery

| | Left Renal Stimulation | | | | | | | |
|---|---|---|---|---|---|---|---|---|
| SBP | Maximal Responses (mmHg) | | | | Minimal Responses (mmHg) | | | |
| Animal No. | Baseline | Maximal | Δ | Stimulation Location | Baseline | Minimal | Δ | Stimulation Location |
| Pig 1 | 131.5 | 151 | 19.5 | AO Side | 140 | 142 | 2 | Renal Side |
| Pig 2 | 155 | 159 | 4 | Renal Side | 155 | 159 | 4 | AO Side |
| Pig 3 | 173 | 202 | 29 | Renal Side | 169 | 170 | 1 | AO Side |
| Average | 153.2 | 170.7 | 17.5 | | 154.7 | 157.0 | 2.3 | |
| SD | 20.8 | 27.4 | 12.6 | | 14.5 | 14.1 | 1.5 | |

TABLE 4B

Changes in Diastolic Blood Pressure (DBP) During Electrical Stimulation in Left Renal Artery

| | Left Renal Stimulation | | | | | | | |
|---|---|---|---|---|---|---|---|---|
| DBP | Maximal Responses (mmHg) | | | | Minimal Responses (mmHg) | | | |
| Animal No. | Baseline | Maximal | Δ | Stimulation Location | Baseline | Minimal | Δ | Stimulation Location |
| Pig 1 | 99 | 108 | 9 | AO Side | 116 | 117 | 1 | Renal Side |
| Pig 2 | 112 | 115 | 3 | Renal Side | 114 | 116 | 2 | AO Side |
| Pig 3 | 119 | 139 | 20 | Renal Side | 110 | 115 | 5 | AO Side |
| Average | 110.0 | 120.7 | 10.7 | | 113.3 | 116.0 | 2.7 | |
| SD | 10.1 | 16.3 | 8.6 | | 3.1 | 1.0 | 2.1 | |

TABLE 4C

Changes in Mean Arterial Pressure (MAP) During Electrical Stimulation in Left Renal Artery

| | Left Renal Stimulation | | | | | | | |
|---|---|---|---|---|---|---|---|---|
| MAP | Maximal Responses (mmHg) | | | | Minimal Responses (mmHg) | | | |
| Animal No. | Baseline | Maximal | Δ | Stimulation Location | Baseline | Minimal | Δ | Stimulation Location |
| Pig 1 | 112.5 | 125 | 12.5 | AO Side | 123 | 128 | 5 | Renal Side |
| Pig 2 | 130 | 133 | 3 | Renal Side | 131 | 132 | 1 | AO Side |
| Pig 3 | 141 | 158 | 17 | Renal Side | 136 | 138 | 2 | AO Side |
| Average | 127.8 | 138.7 | 10.8 | | 130.0 | 132.7 | 2.7 | |
| SD | 14.4 | 17.2 | 7.1 | | 6.6 | 6.0 | 2.1 | |

TABLE 4D

Changes in Heart Rate (HR) During Electrical Stimulation in Left Renal Artery

| | Left Renal Stimulation | | | | | | | |
|---|---|---|---|---|---|---|---|---|
| HR | Maximal Responses (mmHg) | | | | Minimal Responses (mmHg) | | | |
| Animal No. | Baseline | Maximal | Δ | Stimulation Location | Baseline | Minimal | Δ | Stimulation Location |
| Pig 1 | 150 | 151 | 1 | Renal Side | 140 | 130 | −10 | Renal Side |
| Pig 2 | 126 | 132 | 6 | AO Side | 132 | 120 | −12 | Renal Side |
| Pig 3 | 138 | 142 | 4 | Renal Side | 159 | 150 | −9 | AO Side |
| Average | 138.0 | 141.7 | 3.7 | | 143.7 | 133.3 | −10.3 | |
| SD | 12.0 | 9.5 | 2.5 | | 13.9 | 15.3 | 1.5 | |

TABLE 5A

Changes in Systolic Blood Pressure (SBP) During Electrical Stimulation in Right Renal Artery

| | Right Renal Stimulation | | | | | | | |
|---|---|---|---|---|---|---|---|---|
| SBP | Maximal Responses (mmHg) | | | | Minimal Responses (mmHg) | | | |
| Animal No. | Baseline | Maximal | Δ | Stimulation Location | Baseline | Minimal | Δ | Stimulation Location |
| Pig 1 | 151.5 | 156 | 4.5 | Renal Side | 155 | 158 | 3 | AO Side |
| Pig 2 | 153 | 166 | 13 | Renal Side | 157 | 162 | 5 | AO Side |
| Pig 3 | 154 | 167 | 13 | Renal Side | 157 | 162 | 5 | AO Side |
| Average | 152.8 | 163.0 | 10.2 | | 156.3 | 160.7 | 4.3 | |
| SD | 1.3 | 6.1 | 4.9 | | 1.2 | 2.3 | 1.2 | |

TABLE 5B

Changes in Diastolic Blood Pressure (DBP) During Electrical Stimulation in Right Renal Artery

| | Right Renal Stimulation | | | | | | | |
|---|---|---|---|---|---|---|---|---|
| DPB | Maximal Responses (mmHg) | | | | Minimal Responses (mmHg) | | | |
| Animal No. | Baseline | Maximal | Δ | Stimulation Location | Baseline | Minimal | Δ | Stimulation Location |
| Pig 1 | 111.5 | 113 | 1.5 | Renal Side | 113 | 113 | 0 | AO Side |
| Pig 2 | 113 | 119 | 6 | Renal Side | 114 | 117 | 3 | AO Side |
| Pig 3 | 110 | 113 | 3 | Renal Side | 112 | 110 | −2 | AO Side |
| Average | 111.5 | 115.0 | 3.5 | | 113.0 | 113.3 | 0.3 | |
| SD | 1.5 | 3.5 | 2.3 | | 1.0 | 3.5 | 2.5 | |

TABLE 5C

Changes in Mean Arterial Pressure (MAP) During Electrical Stimulation in Right Renal Artery

| MAP | Right Renal Stimulation | | | | | | | |
|---|---|---|---|---|---|---|---|---|
| | Maximal Responses (mmHg) | | | | Minimal Responses (mmHg) | | | |
| Animal No. | Baseline | Maximal | Δ | Stimulation Location | Baseline | Minimal | Δ | Stimulation Location |
| Pig 1 | 130 | 130 | 0 | AO Side | 131 | 130 | −1 | Renal Side |
| Pig 2 | 130 | 141 | 11 | Renal Side | 132 | 135 | 1 | AO Side |
| Pig 3 | 127 | 130 | 3 | Renal Side | 130 | 131 | 1 | AO Side |
| Average | 129.0 | 133.7 | 4.7 | | 131.0 | 132.0 | 1.0 | |
| SD | 1.7 | 6.4 | 5.7 | | 1.0 | 2.6 | 2.0 | |

TABLE 5D

Changes in Heart Rate (HR) During Electrical Stimulation in Right Renal Artery

| HR | Right Renal Stimulation | | | | | | | |
|---|---|---|---|---|---|---|---|---|
| | Maximal Responses (beats/min) | | | | Minimal Responses (beats/min) | | | |
| Animal No. | Baseline | Maximal | Δ | Stimulation Location | Baseline | Minimal | Δ | Stimulation Location |
| Pig 1 | 141 | 146 | 5 | AO Side | 144 | 135 | −9 | Renal Side |
| Pig 2 | 135 | 147 | 12 | Renal Side | 120 | 117 | −3 | AO Side |
| Pig 3 | 129 | 135 | 6 | Renal Side | 126 | 123 | −3 | AO Side |
| Average | 135.0 | 142.7 | 7.7 | | 130.0 | 125.0 | −5.0 | |
| SD | 6.0 | 6.7 | 3.8 | | 12.5 | 9.2 | 3.5 | |

TABLE 6

Possible effect stimulating renal nerves

| Publication | Animal Model | Change of blood pressure when renal nerve stimulated | Change of heart rate when renal nerve stimulated |
|---|---|---|---|
| Ueda H, Uchida Y and Kamisaka K, "Mechanism of the Reflex Depressor Effect by Kidney in Dog", Jpn. Heart J., 1967, 8 (6): 597-606 | Dog | decrease | N/A |
| Beacham WS and Kunze DL, "Renal Receptors Evoking a Spinal Vasometer Reflex", J. Physiol., 1969, 201 (1): 73-85 | Cat | decrease | N/A |
| Aars H and Akre S "Reflex Changes in Sympathetic Activity and Arterial Blood Pressure Evoked by Afferent Stimulation of the Renal Nerve", Acta Physiol. Scand., 1970, 78 (2): 184-188 | Rabbit | decrease | N/A |
| Ma G and Ho SY, "Hemodynamic Effects of Renal Interoreceptor and Afferent Nerve Stimulation in Rabbit", Acta Physiol. Sinica, 1990, 42 (3): 262-268 | Rabbit | decrease | Decrease |
| Lu M, Wel SG and Chal XS, "Effect of Electrical Stimulation of Afferent Renal Nerve on Arterial Blood Pressure, Heart Rate and Vasopressin in Rabbits", Acta Physiol. Sinica, 1995, 47 (5): 471-477 | Rabbit | decrease | Decrease |

Figure 11:
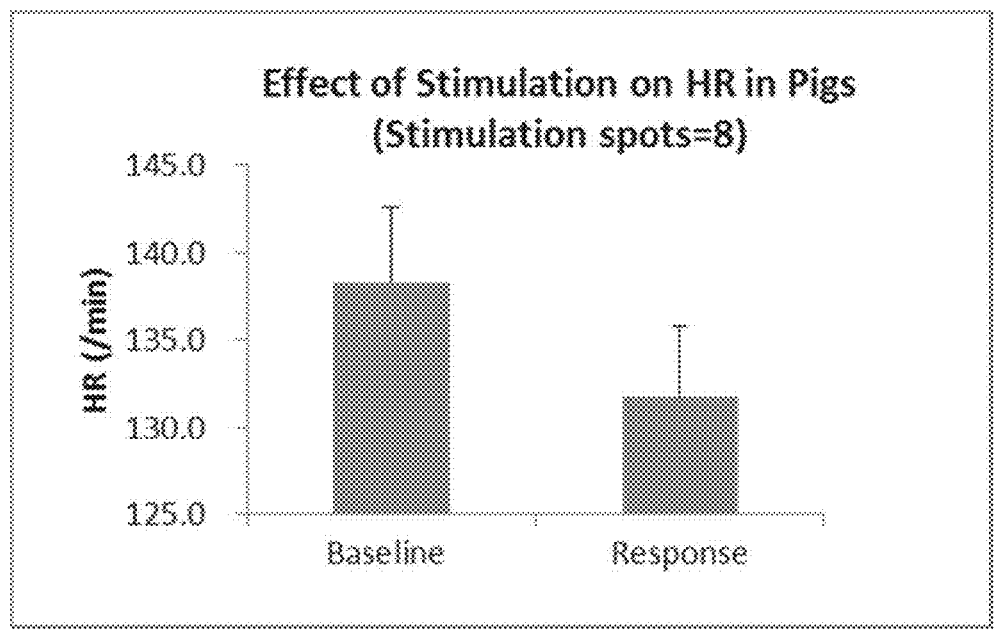
FIG. 11 shows the decreases in heart rate once intra-renal artery stimulations were applied to certain locations of renal artery.
Figure 12A:
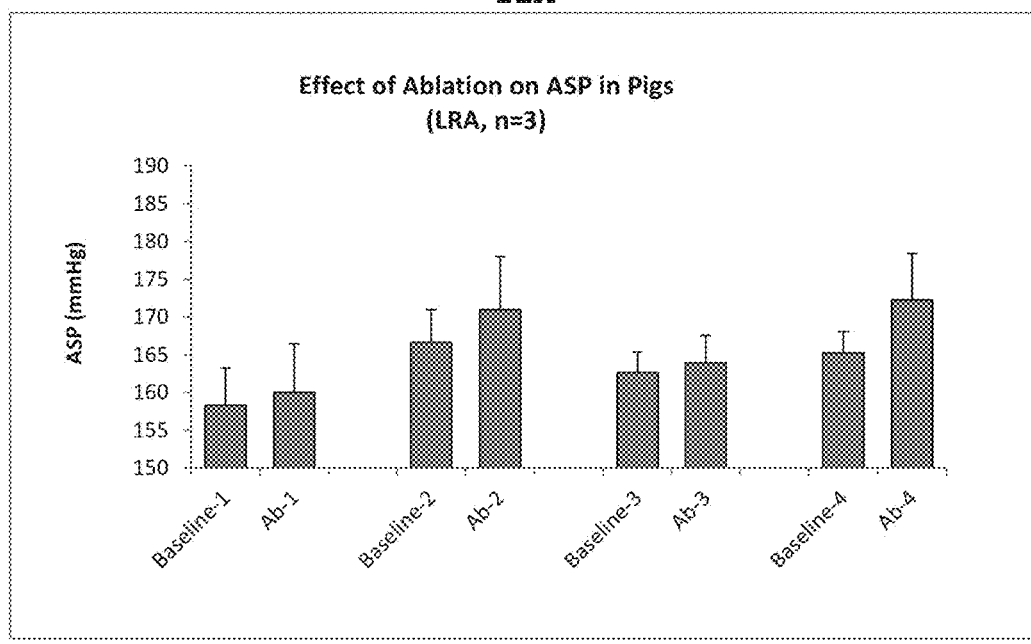
FIG. 12A shows Changes in Arterial Systolic Pressure (ASP) during Four Separated Renal Ablation in Left Renal Artery. Shown are the changes in arterial systolic pressure (ASP, as measured in mmHg) during four separate renal ablations in the left renal artery (LRA).
Figure 12B:
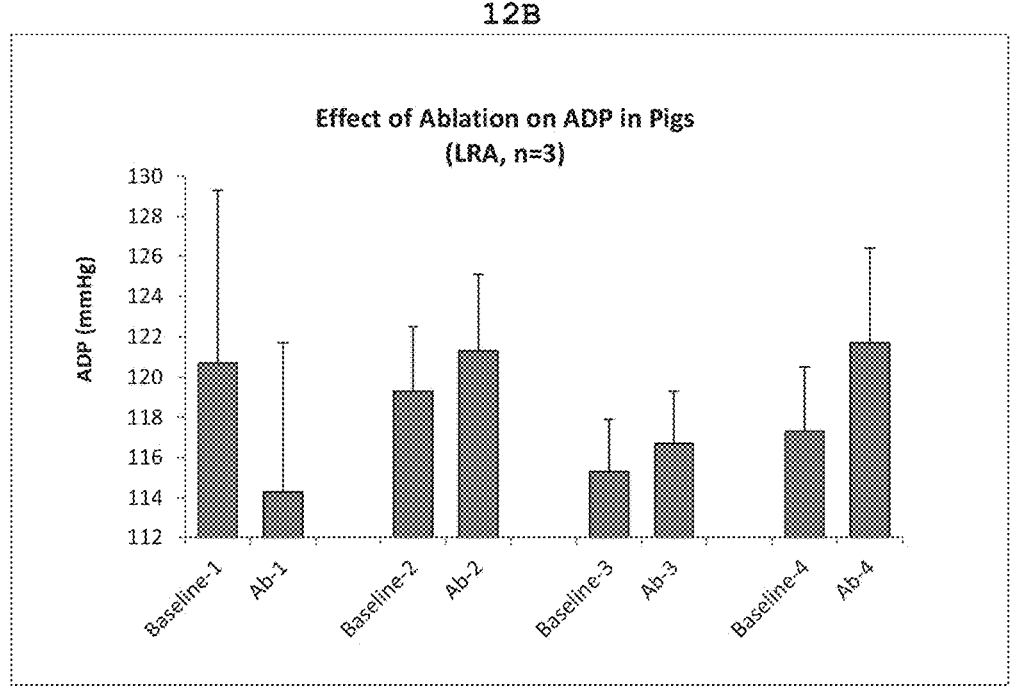
FIG. 12B shows Changes in Arterial Diastolic Pressure (ADP) during Four Separated Renal Ablation in Left Renal Artery. Shown are changes in arterial diastolic pressure (ADP, as measured in mmHg) during four separate renal ablations in the left renal artery (LRA).
Figure 12C:
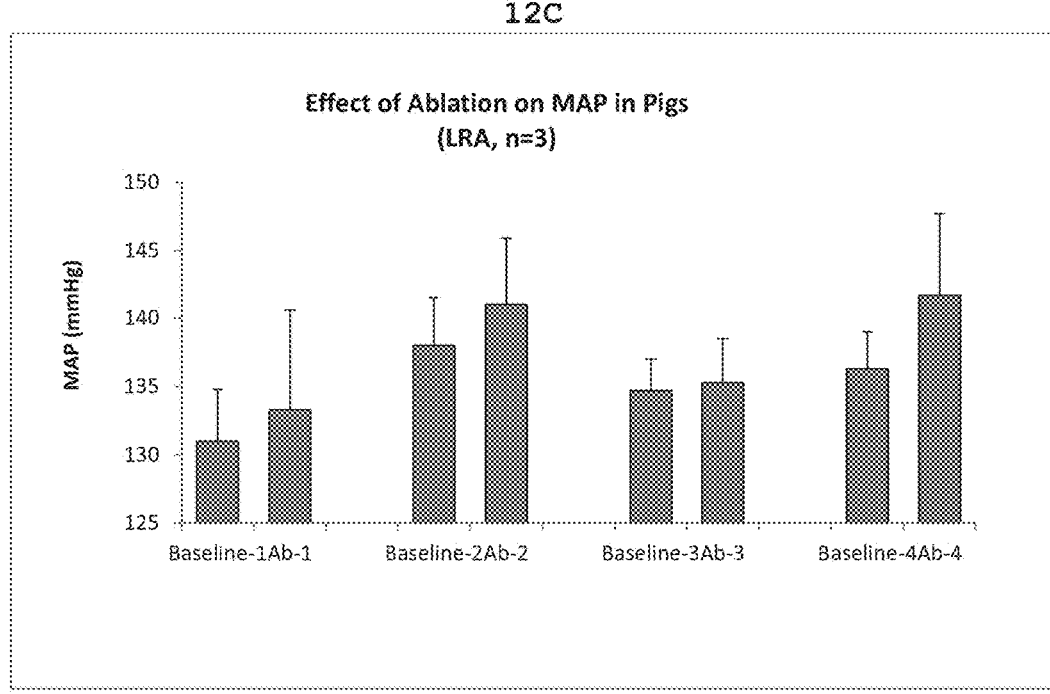
FIG. 12C shows Changes in Mean Arterial Pressure (MAP) during Four Separated Renal Ablation in Left Renal Artery. Shown are changes in mean arterial pressure (MAP, as measured in mmHg) during four separate renal ablations in the left renal artery (LRA).
Figure 12D:
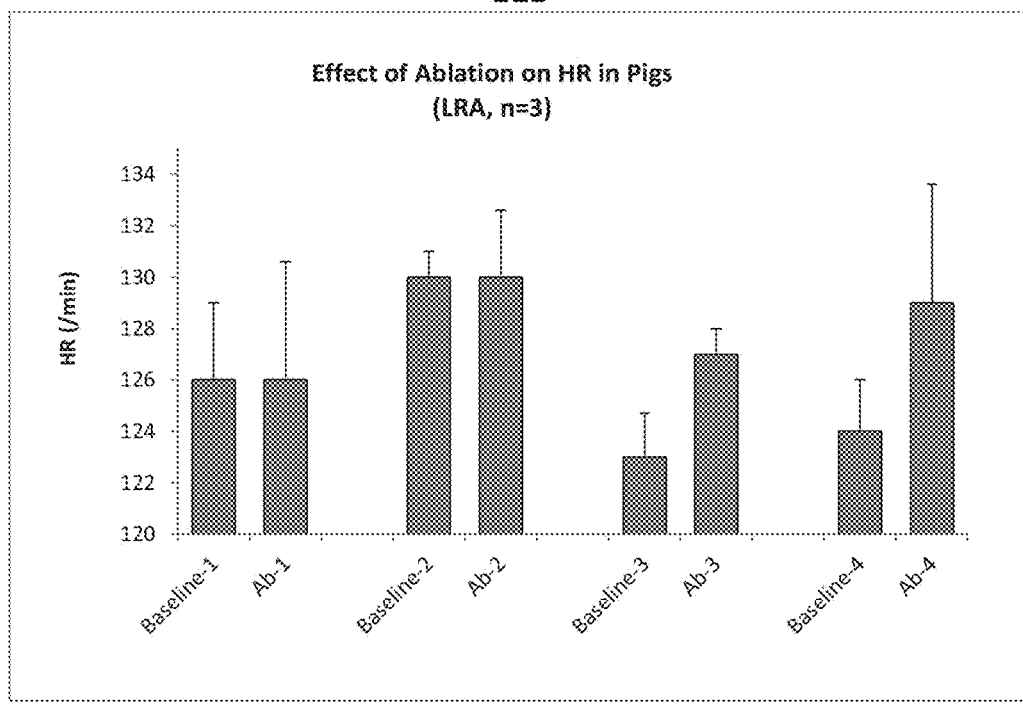
FIG. 12D shows Changes in Heart Rate (HR) during Four Separated Renal Ablation in Left Renal Artery. Shown are changes in heart rate during four separate renal ablations in the left renal artery (LRA).
Figure 13A:
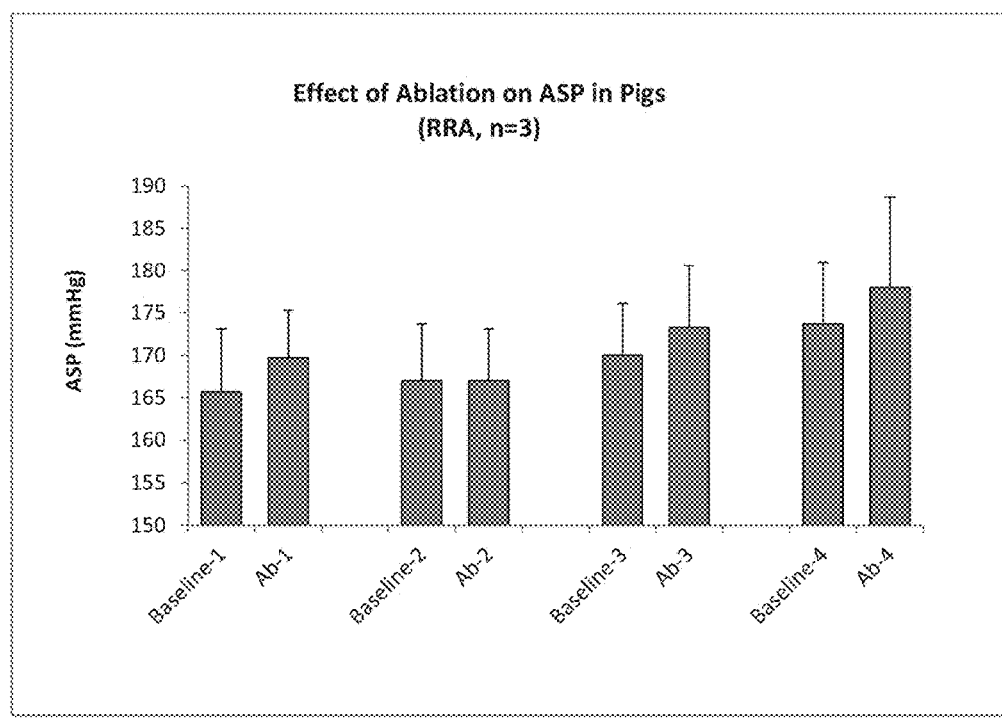
FIG. 13A shows Changes in Arterial Systolic Pressure (ASP) during Four Separated Renal Ablation in Right Renal Artery. Shown are changes in arterial systolic pressure (ASP, as measured in mmHg) during four separate renal ablations in the right renal artery (RRA).
Figure 13B:
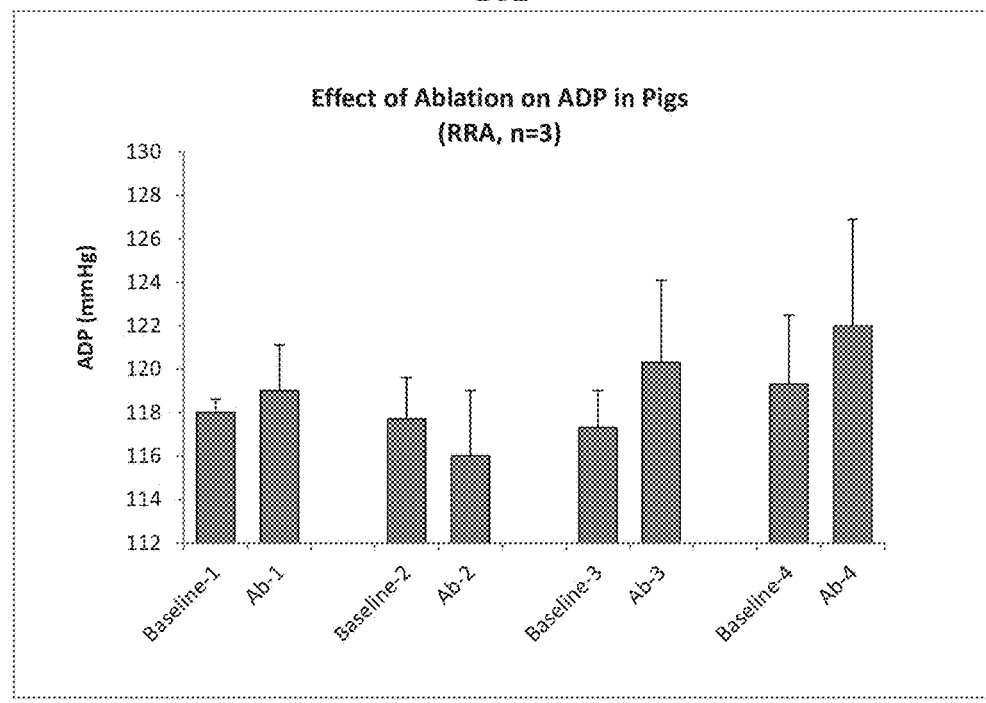
FIG. 13B shows Changes in Arterial Diastolic Pressure (ADP) during Four Separated Renal Ablation in Right Renal Artery. Shown are changes in arterial diastolic pressure (ADP, as measured in mmHg) during four separate renal ablations in the right renal artery (RRA).
Figure 13C:
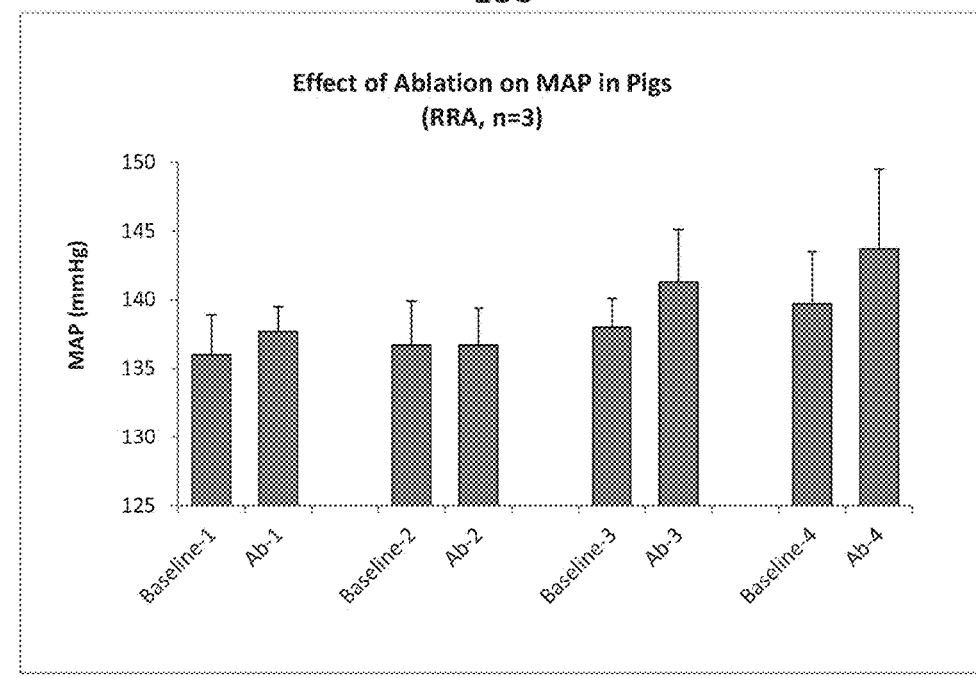
FIG. 13C Changes in Mean Arterial Pressure (MAP) during Four Separated Renal Ablation in Right Renal Artery. Shown are changes in mean arterial pressure (MAP, as measured in mmHg) during four separate renal ablations in the right renal artery (RRA).
Figure 13D:
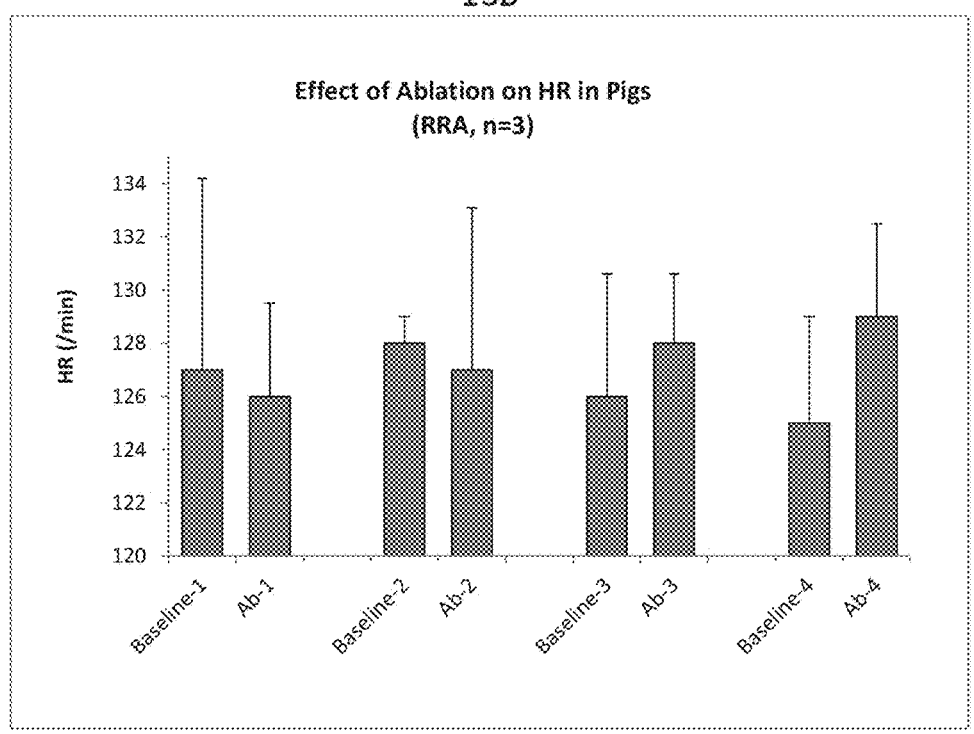
FIG. 13D shows Changes in Heart Rate (HR) during Four Separated Renal Ablation in Right Renal Artery. Shown are changes in heart rate during four separate renal ablations in the right renal artery (RRA).

Among all the stimulation experiments performed in pigs according to the previously described protocol, certain locations in the renal arterial wall led to significant decreases in heart rate without causing changes in the blood pressure or the change in blood pressure is minimal in comparison to the decrease in heart rate (FIG. 11). Slight decreases in blood pressure, especially, diastolic blood pressure were often recorded. Out of the 56 data points inclusive of all 4 physiological parameters evaluated in the experiments, there were at least 1 data point from each physiological parameter that responded with the dose of energy by a drop or no/insignificant change in value; this accounted for over 23% of the data points in this experiment. These distinctive physiological changes in response to the stimulations appear to indicate that nerves innervating these locations are of parasympathetic nature and are different from those sympathetic nerves innervating the locations that results in increases in blood pressure and heart rate upon stimulation.

Table 6 summarized the effect of delivering a suitable dose of energy to the afferent renal nerve in different studies involving animal models of dogs, cats and rabbits. In conjunction with this invention, the studies in Table 6 had demonstrated that it is not uncommon to induce effects akin to parasympathetic activity when a suitable dose of energy is delivered to the nerves innervating the kidney. In other words, there is an indication that, in the neural circuitry of the renal artery, there exist nerves that can induce parasympathetic activity rather than sympathetic activity and therefore should not be ablated when treating blood pressure related diseases.

EXAMPLE 3

Ensuring Energy is Directed to a Target Nerve During Ablation

Subsequent to the studies for locating and identifying nerves in an arterial wall, energies at dosage suitable for ablations were also delivered to the innervated spots in the renal arterial wall of the same pigs. Four ablations were each delivered to the left and to the right renal arteries starting from the kidney side and moving to the abdominal aorta side in the order of movement from the anterior, to the posterior, to the superior and then to the inferior wall; each ablation was ≤5 mm apart from the location of the previous ablation and the electrode head (catheter tip) of the ablation catheter was turned 90 degrees after each ablation. Based on the literature (Krum 2009, 2010), low energy level (5-8 watts) should be used for renal ablation; therefore, 5 watts and 8 watts were used for renal ablation. For left renal artery ablation, the energy level applied was 5 watts and the time length of ablation was 120 seconds; for the right renal artery, the ablation energy level applied was 8 watts and the time length was 120 seconds. The temperature at the ablation site was measured to be from 40° C. to 50° C. The physiological parameters: systolic blood pressure, diastolic blood pressure, mean arterial pressure and heart rate were examined during ablations. The data clearly showed that ablation at different locations within the renal artery resulted in differing changes in blood pressure and heart rate, further demonstrating that changes in physiological parameters such as blood pressure and heart rate can be used as indicators for an accurate delivery of ablation energy to a targeted nerve and provided further evidence that distribution of the nerves in the arterial wall varied case by case.

Changes in systolic blood pressure, diastolic blood pressure, mean arterial pressure and heart rate during four separate renal ablations in the renal arteries of the left kidney were summarized in FIGS. 12A, 12B, 12C and 12D, respectively. Changes in arterial systolic and diastolic pressure, mean arterial pressure and heart rate during four separate renal ablations in the renal arteries of the right kidney were summarized in FIGS. 13A, 13B, 13C and 13D, respectively.

EXAMPLE 4

Chronic Renal Nerve Ablation Experimental Results

Figure 14:
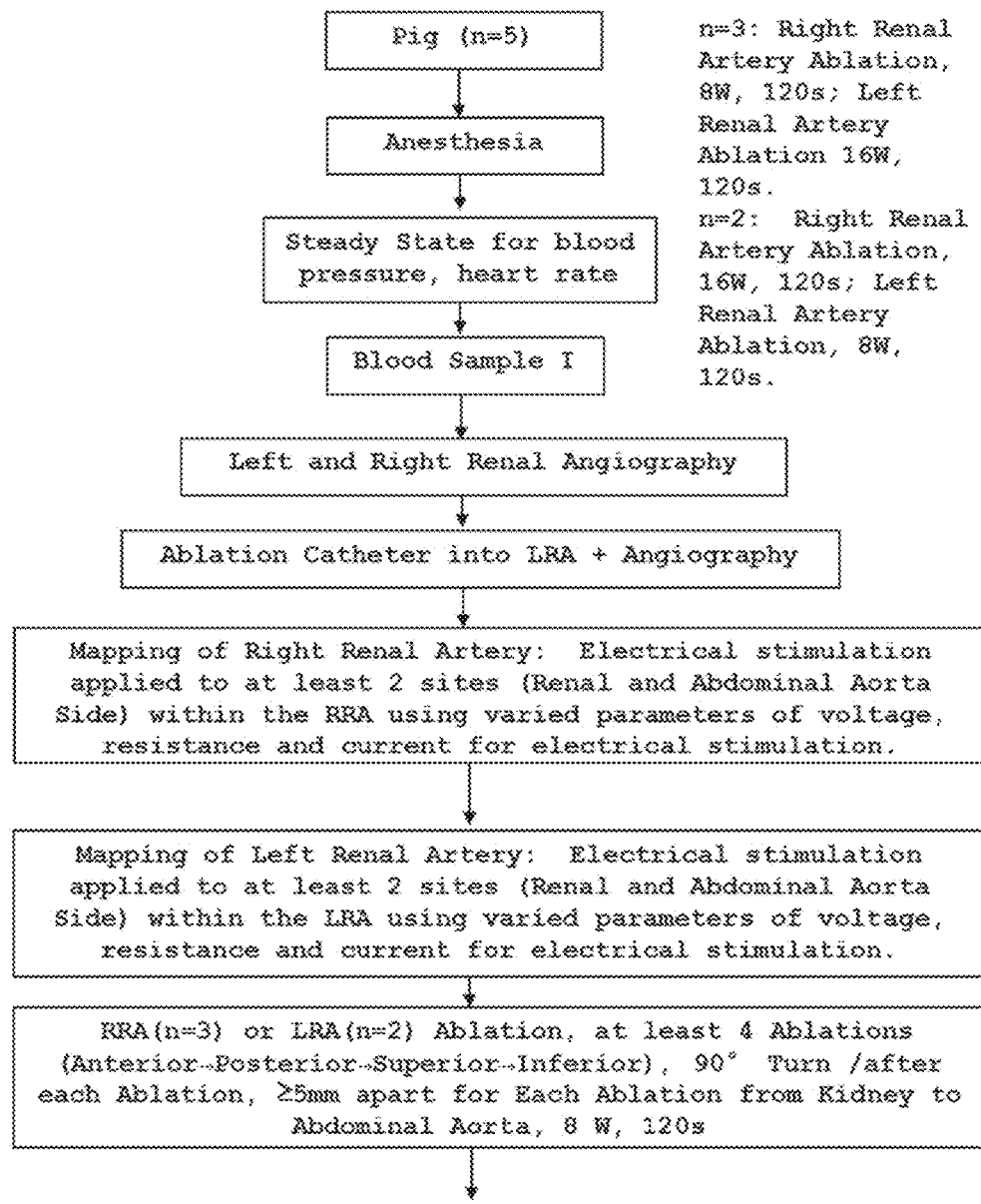
FIG. 14 shows the experimental setup for the chronic renal nerve ablation experiments.

This set of experiments involves methods to determine the safety profile of the energy levels used in existing cardiac ablation catheters in the denervation of renal nerves. FIG. 14 describes the details of this experiment.

The ablation catheter used in this set of experiments was the 7F,B-Type, spacing 2-5-2 mm, CELSIUS® RMT Diagnostic/Ablation Steerable Catheter (Biosense Webster, Diamond Bar, Calif. 91765, USA) and a Celsius radiofrequency generator (STOCKERT 70 RF Generator, Model Stockert GmbH EP-SHUTTLE ST-3205, STOCKERT GmbH, Freiburg, Germany). Four pigs were used in the study.

The energy levels used for the ablations applied were as follows: Right Renal Artery Ablation, 8 W, 120 s; Left Renal Artery Ablation 16 W, 120 s (n=3). Right Renal Artery Ablation, 16 W, 120 s; Left Renal Artery Ablation, 8 W, 120 s (n=3).

Figure 15:
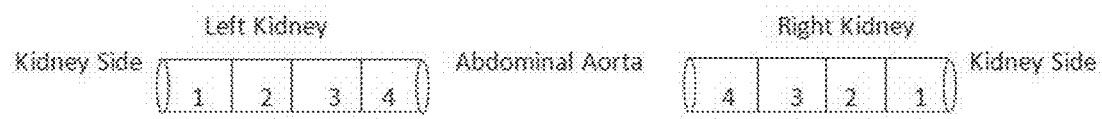
FIG. 15 shows histology map scheme for renal artery sections taken from sacrificed animals.

The pigs were anesthetized, and 4-5 renal ablations were performed for each renal artery (right and left) separately. Renal angiography was performed before and after the ablation to examine the patency of renal arteries. Pigs were allowed to recover from the procedures. In order to determine the safety levels of ablation energy, one pig (Right renal artery, 16 W, 120 s; Left renal artery ablation, 8 W, 120 s) was terminated for assessment of acute lesions due to two different energy levels of ablation. Twelve weeks after the ablation procedure, angiography was performed on the animals for both renal arteries. Thereafter, the animals were sacrificed, and renal arteries and kidneys examined for any visible abnormalities; pictures were taken with renal arteries intact and cut open, with both kidneys cut open longitudinally. Samples from both renal arteries were collected for further histology studies according to the histology maps shown in FIG. 15.

EXAMPLE 5

Renal Mapping Catheter Designs

New catheters designed with functions of stimulation, mapping, ablation and angiography are hereby disclosed.

The catheter apparatus comprises an elongated catheter having a catheter tip on the distal end which, once inserted, is intended to remain in a static position within the renal vascular architecture; a proximal end; and a plurality of ablation electrodes. In one embodiment, the ablation electrodes are evenly-spaced down the length of the elongated catheter tip. The plurality of these ablation electrodes are spaced from the proximal end and from the distal end of the elongated catheter tip by electrically nonconductive segments. In one embodiment, the first electrode on the tip side of the catheter or on the end side of the catheter can be used as a stimulation reference for any other electrodes to deliver electrical stimulation; alternatively, any one of these electrodes can be used as a reference for other electrodes.

In one embodiment, the elongated catheter tip is of a helical shape.

In another embodiment, one or more conducting wires are coupled with and supplying direct or alternating electrical current to the plurality of electrodes via one or more conducting wires. A controller is configured to control the electrical current to the plurality of electrodes in either an independent manner, or a simultaneous manner while the catheter tip remains in a static position in the renal artery.

In another embodiment, one or more conducting wires are coupled with and supplying radiofrequency (RF) energy to the plurality of electrodes, the RF energy being either unipolar RF energy or bipolar RF energy. A radiofrequency generator supplies energy via the one or more conducting wires to the plurality of electrodes. A controller is configured to control the energy source to supply energy to the plurality of electrodes in either an independent manner, a sequential manner, or a simultaneous manner while the catheter tip remains in a static position in the renal artery The RF energy sent to the electrodes may be controlled so that only low-level electrical energy impulses are generated by the electrodes in order to merely stimulate underlying nerve tissue, and in particular, renal nerve tissue. Alternately, the RF energy sent to the electrodes may be controlled so that greater electrical energy impulses are generated by the electrodes in order to ablate underlying nerve tissue, and in particular, renal nerve tissue. The catheter tip, and in particular, the electrodes, are designed to remain in contact with the renal artery lumen, in the same place, throughout stimulation and ablation In another embodiment, the catheter is capable of being used with radiofrequency generators currently utilized in the practice of cardiac tissue ablation. These radiofrequency generators may include, but are not necessarily limited to those currently produced by Medtronic, Cordis/Johnson & Johnson, St. Jude Medical, and Biotronic.

Exemplary embodiments of the invention, as described in greater detail below, provide apparatuses for renal nerve denervation FIGS. 3 to 7 are examples and illustrations of these ablation catheter and electrodes. Shown are elevational, cross-sectional, and end-on views of a distal portion of the ablation catheter tip according to various embodiments of the present invention.

In one embodiment, the catheter has an elongated tip of a helical shape. A plurality of electrodes is evenly spaced starting from their placement at the proximal end of the catheter tip through the distal end of the catheter tip by electrically nonconductive segments.

In certain embodiments, the catheter tip of the ablation catheter comprises a single helix; in others, it is composed of a double helix. The coil or coils of the helix or helices of the catheter tip may be either round or flat. Electrodes may be placed evenly down the length of the coils; for example, they can be spaced either 60°, 90° or 120° apart, but may be placed in other conformations or separated by different degrees In one embodiment, the electrodes may be either flat and rectangular or square in shape, if the coil of a helix is itself flattened. Alternately, the electrodes may be round and/or built into the helix if the coil is itself round. In another embodiment, the catheter tip has a length of from 2.0 cm to 8.0 cm and a diameter of 0.5 mm to 10.0 mm; the diameters of coil may vary from 3.0 mm to 7.5 mm; the distances of each coil may vary from 4 mm to 6 mm; and the fully uncoiled lengths of the coils may vary from 31 mm to 471 mm; the catheter's total length is from 1 m to 2.0 m.

In another embodiment, the catheter tip of the ablation catheter comprises a balloon catheter system. In one embodiment, electrodes are evenly spaced at intervals along a helical coil which is either round or flat in shape and wrapped around the balloon; in other embodiments, electrodes are spaced along an umbrella frame apparatus which is either round or flat in shape and wrapped down the length of the balloon. In certain embodiments, the umbrella frame apparatus has an open end and in others, a closed end. The electrodes will come into contact with the renal architecture upon inflation of the balloon apparatus. In one embodiment, the catheter tip has a length of 2.0 cm to 8.0 cm and a diameter from 0.5 mm to 10.0 mm when the balloon is not inflated; the diameters of coil may vary from 3.0 mm to 8 mm; the distances of each coil may vary from 4 mm to 6 mm; the numbers of coils may vary from 3.3 to 20; and the fully uncoiled lengths of the coils may vary from 31 mm to 471 mm. the catheter's total length is from 1 m to 2.0 m.

In one embodiment, the diameter of the catheter tip when the balloon is inflated may range from 0.5 mm to 10 mm. The diameter of the coil around the balloon may range from 3 mm to 10 mm and the diameter of a fully inflated balloon is from 3 mm to 10 mm.

The invention may also comprise a catheter tip which is tube-like, cylindrical, and self-expanding with adjustable sizes. The materials used for these catheter tips may, in certain embodiments, comprise nickel-titanium (nitinol) alloy.

In one embodiment of this invention, there is provided a renal nerve modulation and ablation processes (on either the left side kidney, right side kidney, or both) comprising insertion of one of the catheters described above into either the left renal artery (LRA) or the right renal artery (RRA) followed by renal nerve mapping as substantially described above, followed by targeted ablation by individual electrodes.

In one embodiment, nerve stimulation takes place by application of the following parameters: 0.1 ms-20 ms, 2V-30V, 5 mA-40 mA, and 100 Ohm-1000 Ohm. In one embodiment, nerve ablation takes place by application of the following parameters: below 12 watts and 30 seconds-180 seconds.

REFERENCES

1. Aars, H. and Akre, S., (1970), Reflex Changes in Sympathetic Activity and Arterial Blood Pressure Evoked by Afferent Stimulation of the Renal Nerve, Acta Physiol. Scand., 78 (2): 184-188
2. Beacham, W. S. and Kunze, D. L., (1969), Renal Receptors Evoking a Spinal Vasometer Reflex, J. Physiol., 201 (1): 73-85
3. Campese, V. M., Kogosov, E., (April 1995), Renal afferent denervation prevents hypertension in rats with chronic renal failure, 25(4 Pt. 2): 878-882.
4. Campese, V. M., and Krol, E., (June 2002), Neurogenic factors in renal hypertension, Current Hypertension Reports, 4(3):256-260.
5. Converse, R. L. Jr., Jacobsen, T. N., Toto, R. D., Jost, C. M., Cosentino, F., Fouad-Tarazi, F., Victor, R. G., (December 1992) Sympathetic overactivity in patients with chronic renal failure, New England Journal of Medicine, 327(27):1912-1918.
6. Dibona, Gerald F. and Ulla C. Kopp, (January 1997), Neural Control of Renal Function, Physiological Reviews, 77(1): 75-197.
7. DiBona, G. F. (2003), Neural control of the kidney: past, present and future, Hypertension, 41: 621-624.
8. Esler, M., Jennings, G., Lambert, G., Meredith, I., Horne, M., Eisenhofer, G., (October 1990) Overflow of catecholamine neurotransmitters to the circulation: source, fate, and functions, Physiological Reviews, 70(4):963-985.
9. Esler, M., Schlaich, M., Sobotka, P. et al., (2009) Catheter-based renal denervation reduces total body and renal noradrenaline spillover and blood pressure in resistant hypertension, Journal of Hypertension, 27(suppl 4):s167.
10. Esler, M. et al., (Dec. 4, 2010), Renal sympathetic denervation in patients with treatment-resistant hypertension (The Symplicity HTN-2 Trial): a randomized controlled study, The Lancet, 376: 1903-1909.
11. Krum, H., Schlaich, M., Whitbourn, R., Sobotka, P. A., Sadowski, J., Krzysztof, Bartus, K., Kapelak, B., Walton, A., Sievert, H., Thambar, S., Abraham, W. T., and Esler, M., (April 2009), Catheter-based renal sympathetic denervation for resistant hypertension: a multicentre safety and proof-of-principle cohort study, The Lancet, 373 (9671):1275-1281.
12. Lu, M., Wei, S. G. and Chai, X. S., (1995), Effect of Electrical Stimulation of Afferent Renal Nerve on Arterial Blood Pressure, Heart Rate and Vasopressin in Rabbits, Acta Physiol. Sinica, 47 (5): 471-477.
13. Ma, G. and Ho, S. Y., (1990), Hemodynamic Effects of Renal Interoreceptor and Afferent Nerve Stimulation in Rabbit, Acta Physiol. Sinica, 42 (3): 262-268.
14. Mahfoud, F., Schlaich, M., Kindermann, I., Ukena, C., Cremers, B., Brandt, M. C., Hoppe, U. C., Vonend, O., Rump, L. C., Sobotka, P. A., Krum, H., Esler, M., and Böhm, M., (May 10, 2011), Effect of Renal Sympathetic Denervation on Glucose Metabolism in Patients With Resistant Hypertension: A Pilot Study, Circulation 123 (18): 1940-1946.
15. Medical devices: pg 1-2, Feb. 22, 2012
16. Schlaich, M. P., Sobotka, P. A., Krum, H., Lambert, E., and Esler, M. D., (Aug. 27, 2009), New England Journal of Medicine, 36(9): 932-934.
17. Schlaich, M. P., Krum, H., Whitbourn, R. et al., (2009), A novel catheter based approach to denervate the human kidney reduces blood pressure and muscle sympathetic nerve activity in a pateitn with end stage renal disease and hypertension. Journal of Hypertension, 27(suppl 4):s154.
18. Smithwick, R. H., and Thompson, J. E., (Aug. 15, 1953), Splanchnicectomy for essential hypertension; results in 1,266 cases. J Am Med Association, 152(16):1501-1504.
19. Talenfeld, A. D., Schwope, R. B., Alper, H. J., Cohen, E. I., and Lookstein, R. A., (June 2007), MDCT Angiography of the Renal Arteries in Patients with Atherosclerotic Renal Artery Stenosis: Implications for Renal Artery Stenting with Distal Projection, American Journal of Roentgenology, 188: 1652-1658.
20. Ueda, H., Uchida, Y., and Kamisaka, K., (1967), Mechanism of the Reflex Depressor Effect by Kidney in Dog, Jpn. Heart J., 8 (6): 597-606.
21. Valente, J. F., Dreyer, D. R., Breda, M. A., Bennett, W. M., (January 2001), Laparoscopic renal denervation for intractable ADPKD-related pain. Nephrology Dialysis Transplantation, 16(1): 160.
22. Vigilance D. W., Mutrie C. J., Yi G. H., Yu K., Guo A., Gelfand M., Smith C. R, Oz M. C., Levin H., Wang J., (2005), A novel approach to increase total urine output in acute heart failure: unilateral renal nerve blockade. Journal of the American College of Cardiology Supplement 2005, 45(3):166A.
23. Wang, J., Mapping sympathetic nerve distribution for renal ablation and catheters for the same, US patent application no. 2011/0306851 A1, filed Aug. 26, 2011.
24. Ye, S., Zhong, H., Yanamadala, V., Campese, V. M., (August 2002), Renal injury caused by intrarenal injection of phenol increases afferent and efferent sympathetic nerve activity, American Journal of Hypertension, 15(8): 717-724.

What is claimed is:

1. A method of mapping a parasympathetic renal nerve, comprising the steps of:
    a) introducing a catheter into the lumen of a renal artery such that a tip of said catheter contacts a site on an inner wall of said renal artery;
    b) measuring one or more physiological parameters to obtain baseline measurements before introducing an electrical current to the site, said physiological parameters are selected from the group consisting of systolic blood pressure, diastolic blood pressure, mean arterial pressure, and heart rate;
    c) applying electrical stimulation by introducing said electrical current to the site via the catheter, wherein said electrical current is controlled to be sufficient to elicit changes in said physiological parameters when there is an underlying parasympathetic nerve at the site; and
    d) measuring said physiological parameters at a specific time interval after each electrical stimulation, wherein a decrease of said physiological parameters below the baseline measurements after said electrical stimulation would indicate that a parasympathetic renal nerve has been mapped at said site.

2. The method of claim 1, wherein said catheter is an ablative catheter designed to treat cardiac arrhythmias.

3. The method of claim 1, wherein said catheter is an ablative catheter designed specifically for mapping renal nerves for ablative procedures.

4. The method of claim 1, wherein said specific time interval in step (d) is from about 5 seconds to about 2 minutes.

5. The method of claim 1, wherein said one or more physiological parameters includes said systolic blood pressure, and said decrease in systolic blood pressure is more than 2 mmHg.

6. The method of claim 1, wherein said one or more physiological parameters includes said diastolic blood pressure, and said decrease in diastolic blood pressure is more than 2 mmHg.

7. The method of claim 1, wherein said one or more physiological parameters includes said mean arterial pressure, and said decrease in mean arterial pressure is more than 2 mmHg.

8. The method of claim 1, wherein said one or more physiological parameters includes said heart rate, and said decrease in heart rate is more than 5 beats/min.

9. The method of claim 1, wherein the electrical current sufficient to elicit changes in the physiological parameters comprises one or more of the following parameters:
    (a) voltage of between 2 and 30 volts;
    (b) resistance of between 100 and 1000 ohms;
    (c) current of between 5 and 40 miliamperes; or
    (d) applied between 0.1 and 20 milliseconds.

10. The method of claim 1, further comprising a step of applying radiofrequency energy through the catheter for ablation of underlying nerve to treat disease caused by systemic renal nerve hyperactivity, wherein said ablation is not applied to the site identified in step (d).

11. A method of mapping a sympathetic renal nerve, comprising the steps of:
    a) introducing a catheter into the lumen of a renal artery such that a tip of said catheter contacts a site on an inner wall of said renal artery;
    b) measuring one or more physiological parameters to obtain baseline measurements before introducing an electrical current to the site, said physiological parameters are selected from the group consisting of systolic blood pressure, diastolic blood pressure, mean arterial pressure, and heart rate;
    c) applying electrical stimulation by introducing said electrical current to the site via the catheter, wherein said electrical current is controlled to be sufficient to elicit changes in said physiological parameters when there is an underlying sympathetic nerve at the site; and d) measuring said physiological parameters at a specific time interval after each electrical stimulation, wherein an increase of said physiological parameters below the baseline measurements after said electrical stimulation would indicate that a sympathetic renal nerve has been mapped at said site.

12. The method of claim 11, wherein said catheter is an ablative catheter designed to treat cardiac arrhythmias.

13. The method of claim 11, wherein said catheter is an ablative catheter designed specifically for mapping renal nerves for ablative procedures.

14. The method of claim 11, wherein said specific time interval in step (d) is from about 5 seconds to about 2 minutes.

15. The method of claim 11, wherein said one or more physiological parameters includes said systolic blood pressure, and said increase in systolic blood pressure is more than 4 mmHg.

16. The method of claim 11, wherein said one or more physiological parameters includes said diastolic blood pressure, and said increase in diastolic blood pressure is more than 1.5 mmHg.

17. The method of claim 11, wherein said one or more physiological parameters includes said mean arterial pressure, and said increase in mean arterial pressure is more than 3 mmHg.

18. The method of claim 11, wherein said one or more physiological parameters includes said heart rate, and said increase in heart rate is more than 4 beats/min.

19. The method of claim 11, wherein the electrical current sufficient to elicit changes in the physiological parameters comprises one or more of the following parameters:
   (a) voltage of between 2 and 30 volts;
   (b) resistance of between 100 and 1000 ohms;
   (c) current of between 5 and 40 miliamperes; or
   (d) applied between 0.1 and 20 milliseconds.

20. The method of claim 11, further comprising a step of applying radiofrequency energy through the catheter to the site identified in step (d) for ablation of said sympathetic renal nerve to treat disease caused by systemic renal nerve hyperactivity.

* * * * *